United States Patent
Speck et al.

(10) Patent No.: US 9,265,580 B2
(45) Date of Patent: Feb. 23, 2016

(54) SPECIMEN OBSERVATION, COLLECTION, STORAGE AND PRESERVATION DEVICES AND METHODS OF USE

(71) Applicants: Jonathan M. Speck, Memphis, TN (US); Ronald L Speck, Memphis, TN (US); Glenda Beth Horn Herring, Gulf Breeze, FL (US); Diana K Faugno, Palm Desert, CA (US); Rachell A Ekroos, Henderson, NV (US); Stacey A. Mitchell, Magnolia, TX (US); Erik J. Ernst, San Diego, CA (US); John M. Hawkins, Covington, GA (US)

(72) Inventors: Jonathan M. Speck, Memphis, TN (US); Ronald L Speck, Memphis, TN (US); Glenda Beth Horn Herring, Gulf Breeze, FL (US); Diana K Faugno, Palm Desert, CA (US); Rachell A Ekroos, Henderson, NV (US); Stacey A. Mitchell, Magnolia, TX (US); Erik J. Ernst, San Diego, CA (US); John M. Hawkins, Covington, GA (US)

(*) Notice: Subject to any disclaimer, the term of this patent is extended or adjusted under 35 U.S.C. 154(b) by 0 days.

(21) Appl. No.: 14/267,818

(22) Filed: May 1, 2014

(65) Prior Publication Data

US 2014/0330167 A1    Nov. 6, 2014

Related U.S. Application Data

(60) Provisional application No. 61/818,070, filed on May 1, 2013.

(51) Int. Cl.
*A61B 10/00* (2006.01)
*A61B 19/02* (2006.01)
*A61B 10/02* (2006.01)

(52) U.S. Cl.
CPC ........... *A61B 19/026* (2013.01); *A61B 10/0058* (2013.01); *A61B 10/0291* (2013.01); *A61B 2010/0006* (2013.01); *A61B 2010/009* (2013.01); *A61B 2010/0074* (2013.01); *A61B 2010/0216* (2013.01)

(58) Field of Classification Search
CPC .................................................. A61B 19/026
USPC .......... 600/562–569, 572, 463; 128/837, 838; 436/63, 94; 435/304.1, 307.1, 309.1, 435/6.12, 287.2; 604/1
See application file for complete search history.

(56) References Cited

U.S. PATENT DOCUMENTS

| | | | | |
|---|---|---|---|---|
| 4,136,680 A * | 1/1979 | Southworth | ............... | 600/572 |
| 5,787,891 A * | 8/1998 | Sak | ............... | 600/569 |
| 6,352,513 B1 * | 3/2002 | Anderson et al. | ............... | 600/572 |
| 7,165,550 B1 * | 1/2007 | Tracy et al. | ............... | 128/837 |
| 2005/0288606 A1* | 12/2005 | Alter | ............... | 600/572 |
| 2007/0207549 A1* | 9/2007 | Sangha et al. | ............... | 436/63 |
| 2008/0188769 A1* | 8/2008 | Lu | ............... | 600/569 |
| 2011/0270091 A1* | 11/2011 | Hossack et al. | ............... | 600/463 |
| 2013/0115607 A1* | 5/2013 | Nielsen et al. | ............... | 435/6.12 |

* cited by examiner

*Primary Examiner* — Brian Szmal
(74) *Attorney, Agent, or Firm* — Hulsey Hunt & Parks, P.C.

(57) ABSTRACT

The devices and methods taught in this disclosure are directed to facilitate the observation, collection, transportation, storage, and preservation of specimens possibly containing DNA, said specimens potentially constituting evidence of sexual assault. The devices and methods described further allow for a means of minimizing the possibility of specimen contamination, dilution, or degradation during the collection and storage processes. The disclosed devices may contain electrical components that provide for the generation and recordation of information (specifically, times, dates, and locations) related to circumstances surrounding the collection of such specimens. This information may serve as evidence corroborating the circumstance of specimen collection, it may help to maintain a known and identifiable Chain of Custody (CoC), and it may additionally be used for unique device identification (UDI), inventory control, and current procedural terminology (CPT) coding purposes.

27 Claims, 21 Drawing Sheets

FIG 15

Ancillaries

Supplies
99070

Venipuncture
36415

Nasal Cavity

Rhinoscope, removal foreign body
30300

Ear

Otoscope with removal foreign body
69200

Oral Cavity

Oral swap can be billed though path (inclusive to E&M code with removal foreign body)

Colposcopy

Colposcopy, vulva
56820

Colposcope, entire vagina and cervix if present
57420

Colposcope, w/ removal of foreign body is inclusive w/ E&M

Anoscopy

Anoscopy w/ or w/o collection
46600

Anoscopy with removal foreign body
46608

Anoscopy, (HRA) High resolution with magnification, w/ or w/o specimen collection
0226T Evaluation of Patient Emergency Room
99281-99285

Established Office/Output
99211-99215

New Office/ Output
99201-99205

Hospital Administration
99221-99223

Medical services after regularly scheduled hours
99050

Medical services between hours of 10pm-8am (at 24 hr Facility)
99053

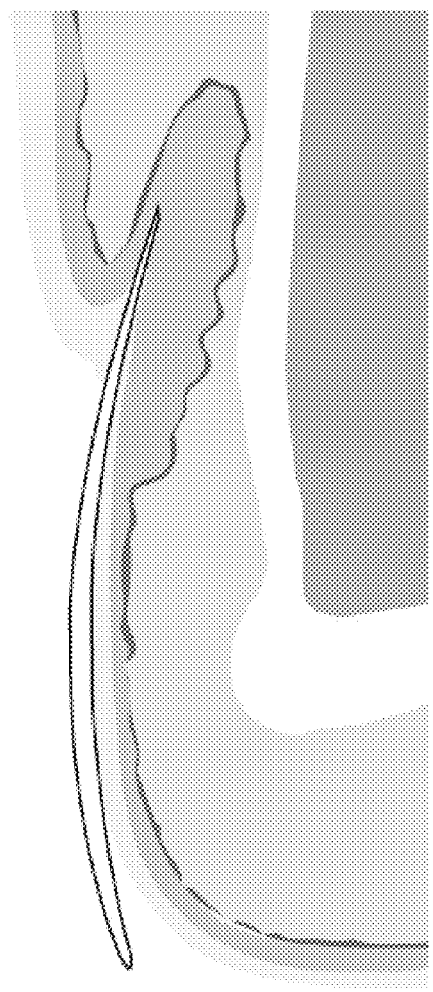
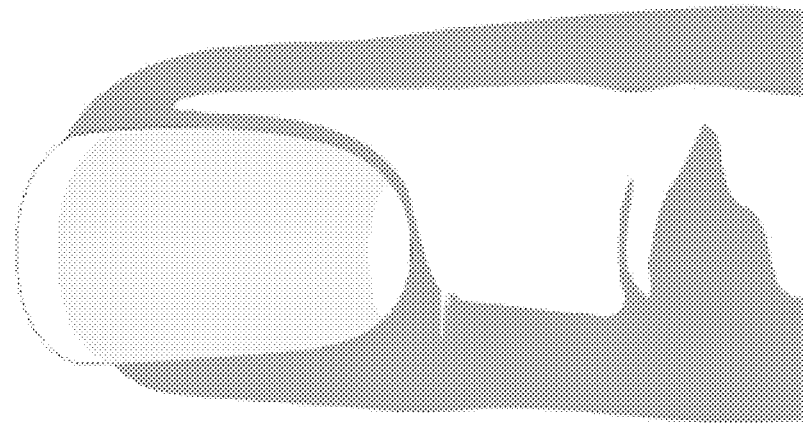
FIG 19B
FIG 19A

SPECIMEN OBSERVATION, COLLECTION, STORAGE AND PRESERVATION DEVICES AND METHODS OF USE

CROSS-REFERENCE TO RELATED APPLICATIONS

This application claims priority to U.S. Provisional Patent Application Ser. No. 61/818,070, filed May 1, 2013, which is hereby incorporated by reference in its entirety.

FIELD OF THE INVENTION

The present disclosure relates to devices for the observation, collection, storage, and preservation of specimens and the methods of their use. More precisely, the present disclosure relates to devices and the methods of their use for the observation, collection, storage, and preservation of specimens that may constitute evidence, including, but not limited to, biologic specimens that may contain deoxyribonucleic acid (DNA), and/or non-biological materials that may include chemical elements, including minerals and yet unknown particles. The disclosed devices and methods further provide for the incorporation of electrical circuits that may identify, record, and transmit information related to the device's use, for the purposes of corroborating specimen collection, and means for device identification and tracking for facilitating chain of custody (CoC) creation and maintenance, current procedural terminology (CPT) coding, inventory control, and for complying with unique device identification (UDI) regulations as set forth by the United States Food and Drug Administration (FDA). The specimens collected may be part of evidence related to crimes specifically including, but not limited to, sexual assault. Additionally, the specimens collected may provide diagnostic testing as part of a woman's well woman exam or in order to diagnose a sexually transmitted infection related to a gynecological complaint.

BACKGROUND OF THE INVENTION

For the purposes of clarity, when interpreting the disclosure contained in this document, several terms will be defined before their use. When used herein "sexual assault" is to be interpreted broadly in order to encompass rape and sexual assault as defined by the Bureau of Justice Statistics whose definitions are to follow. According to the Bureau of Justice Statistics, "rape" is defined as "[f]orced sexual intercourse including both psychological coercion as well as physical force. Forced sexual intercourse means penetration by the offender(s). Includes attempted rapes, male as well as female victims, and both heterosexual and homosexual rape"; and "sexual assault" is defined as "[a] wide range of victimizations, separate from rape or attempted rape. These crimes include attacks or attempted attacks generally involving unwanted sexual contact between victim and offender". This definition of sexual assault as it is used in the disclosure made herein should be considered to further include any of the aforementioned events perpetrated against gay, bisexual, lesbian, transgendered, and questioning (GBLTQ) individuals. The term "evidence", when used herein, should be interpreted so as to include any material that may provide for specimens that may potentially contain either DNA or other information that may be pertinent to a controversy. The term "degradation", as used in this disclosure, should be interpreted as any loss of integrity or quality. Additionally, for the purposes of interpreting the disclosure made herein, the terms "component" and "module", or derivations thereof, as well as "sample" and "specimen", or derivations thereof, are used interchangeably and should be considered synonymous.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Specimens, including those that may include DNA, may be retrieved from one or more of any number of areas including, but not limited to, body cavities for some time following their deposition or exchange, and from environments with non-biological chemical elements, including but not limited to areas outside the body. Specimens containing DNA obtained immediately after, or proximate to, an incident stand the highest chances of producing meaningful results; however, despite this, specimens obtained up to one week after their deposition still may have up to approximately an 80% chance of producing a positive result for present DNA using state of the art analysis technology (e.g. enhanced Y-chromosome short tandem repeat (Y-STR) analysis, etc.). The chances of successful collection of viable DNA from these specimens decline at a rate of approximately 20% for each week that passes between specimen deposition and collection. As a result of continuing improvements in DNA analysis, it is possible that specimens obtained even 4 weeks following an incident still have a 20% chance of yielding viable DNA that could be analyzed in order to yield a DNA profile.

Locard's principle holds that the perpetrator of a crime will bring something into the crime scene and leave with something from it, and that any materials exchanged in such a manner may be used as forensic evidence. Should bodily fluids containing DNA of the perpetrator be deposited in, on, and/or near a victim, to increase the likelihood that authorities may identify a perpetrator, evidence should be collected in a timely fashion without dilution or contamination. Furthermore, the collected specimen must remain non-diluted and contaminant-free, while maintained and handled within a regimented, identifiable, and documented chain of custody (CoC) until analysis, in accordance with standard operating procedure (SOP), may be completed. The device(s) used to collect all relevant specimen(s) may additionally comport with current and forthcoming Unique Device Identification (UDI) regulations as defined by the United States Food and Drug Administration (FDA).

Few people who are victims of sexual assault possess the training to successfully collect a specimen from their own body that could potentially contain a sexual assault perpetrator's DNA. Additionally, even if a victim of a sexual assault knows how to collect a specimen that may contain DNA, it is unlikely that they will have immediate access to tools for specimen collection and preservation at, or immediately following, the time of the assault. Furthermore, devices currently employed in the art are not constructed for self-collection by the victim, but rather for use by a qualified, trained medical professional in a setting that has specialized exam tables and other apparatus. This, combined with the awkward ergonomics of these devices in the self-collection context, make self-collection of such specimens difficult, if not impossible.

Frequently, a specimen becomes contaminated through the collection process itself, rendering that evidence of little to no use. Contamination may obscure or obliterate a perpetrator's potential identification. Specimens may become contaminated, diluted, or suffer degradation despite being collected in a timely and skillful manner if the specimen is not transported, handled, stored, and analyzed effectively.

Packaging, handling, transportation, and/or storage of collected specimens are usually necessary before the collected specimen can be tested, examined, and otherwise analyzed in accordance with SOPs. During packaging, handling, transportation, handling, and/or storage, collected specimens may suffer contamination, dilution, or degradation, even if the collected specimens had been properly collected. In court cases where DNA evidence is being introduced, improper or procedurally proper but ineffective methods of storing the DNA evidence may be introduced to challenge the validity of the evidence and/or the associated test results. There are several ways that these can be challenged: a) the methods not being properly followed, b) the results not being properly applied, or c) the current method itself being ineffective. Therefore, it is important to have collected specimens retained in such a manner consistent with standardized policies and procedures for analysis so as to best preserve specimens until such time as described in analysis and storage policies and procedures.

BRIEF SUMMARY OF THE INVENTION

The purpose of this summary is to present integral concepts in a simplified form as a prelude to the more detailed disclosure that is presented herein.

Disclosed herein is an explanation of how to make and use a specimen-collection device for observing, collecting, securing, transporting, and preserving material potentially containing DNA or other information related to a controversy that could potentially constitute evidence of a sexual assault. Embodiments of the specimen-collection device may comprise an outer sheath, an inner sheath, a specimen collector, an actuator, a cap, an actuation mechanism, a circuit, a memory, a processor, a switch, and a power source. The outer sheath may have a generally oblong shape for insertion into a human body cavity and an interior volume inside of which other parts of the specimen-collection device may be retained. The inner sheath may be disposed of inside of the interior volume of the outer sheath, and may be movable such that it may extend partially outside of the inner volume of the outer sheath in a telescoping fashion. The interior volume of the inner sheath may be configured to retain the specimen collector and any specimens it has collected in a sealed environment, while the inner sheath is closed. The specimen collector may be disposed inside of the interior volume of the inner sheath, and may be movable such that it may extend partially outside of the interior volume of the inner sheath in a telescoping fashion. The actuator is a portion of the specimen-collection device that may be operated by the device's user. Actuation of the actuator may cause the actuation mechanism to extend the inner sheath from the interior volume of the outer sheath, with further (or an alternate method of) actuation of the actuator causing the actuation mechanism to open the cap and extend the specimen collector from the interior volume of the inner sheath. The actuation mechanism may also cause the closing of the cap and retraction of the specimen collector and inner sheath, when the actuator is actuated in reverse. The cap may be positioned at the end of the inner sheath. The cap may be openable to allow for the specimen collector to extend from the interior volume of the inner sheath, and it may be closeable to allow for the specimen collector and any collected specimen to be sealed inside of the interior volume of the inner sheath, thereby protecting the collected specimen from contamination, dilution, and/or degradation. The circuit may identify information related to the operation of the specimen-collection device; including information related to the time and date of the specimen-collection device's use, the location where the specimen-collection device was used, and security information. The circuit may identify such information in response to the activation of the switch. Activation of the switch may be triggered by actuation of the actuator, opening and/or closing of the cap, or any number of other actions associated with operation of the specimen-collection device. The processor may take the information identified by the circuit in response to activation of the switch and transfer it to the memory. The memory may record the information identified by the circuit. The power source may provide electrical power, including low-voltage electrical power, to the electronic components of the specimen-collection device.

This disclosure further provides details related to such specimen-collection devices and methods for observing, collecting, handling, transporting, storing, and preserving evidentiary specimens, including those that contain DNA, cellular, or other material, while protecting them from contamination, dilution, or degradation. This disclosure additionally delineates a means for generating, recording, and/or transmitting corroborating evidence related to specimen collection, as well as a means for device identification and tracking to comport with FDA UDI regulation and to assist with CoC validation, current procedural terminology (CPT) coding, and inventory control.

Collected specimens refer specifically to specimens, including but not limited to, specimens of bodily fluids or surfaces potentially having DNA-containing material that may be collected from body cavities, body surfaces, and/or surfaces in the environment. Such specimens may constitute evidence of a sexual assault.

The disclosed devices allow for storage of collected specimens in a manner that protects them from contamination, dilution, and/or degradation. Specimen integrity would thereby be best-maintained by crime scene analysts and/or laboratory personnel using proper packaging, handling, and storage methods in accordance with specimen collection and laboratory SOPs. These specimens could then potentially be available for later forensic or medical analysis, evidentiary use, etc.

Embodiments of this disclosure may be used in conjunction with bona fide scientific methods to collect specimens that may have been deposited in sexual assault victims 6 weeks, or longer prior to its collection, or specimens that may have been deposited on surfaces months prior to their identification and collection.

Some embodiments provide specimen-collection devices comprising a specimen collector, two or more sheaths, and an actuator. The specimen collector defining a longitudinal axis while the inner sheath is disposed about and spaced apart from the specimen collector, and the outer sheath is disposed about the inner sheath. The complete specimen-collection device may be specifically shaped and dimensioned for insertion into a particular body cavity.

The specimen-collection device may be configured as a roughly cylindrical sheath, inside of which one or more additional inner sheaths may be retained. Upon the actuation of an actuator, a portion or more of one or more of the inner sheaths may extend past the terminal end of the outer sheath in a telescoping fashion. An alternate method of actuating the actuator, or other further actuation of the actuator, may cause a specimen collector that is as of yet unexposed to the volume exterior to the most inner sheath to become exposed at the terminal end of the telescoped sheaths. The specimen collector should only be exposed when the terminal end of the telescoped most inner sheath is in proximity (proximity being considered a distance ranging from approximately fractions of an inch to approximately twelve inches) to the specimen collection site. After the specimen has been collected, but while the specimen collector is still in proximity to the specimen collection site, the actuator may be actuated in a reverse manner, causing the retraction of the specimen collector into the interior volume of the most inner sheath. By exposing the specimen collector only while in proximity to the specimen collection site, the user of the device may avoid possible contamination or dilution of the collected specimen during the placement of the device in proximity to the specimen collection site, or removal of the device from the specimen collection site. Once the specimen collector is retracted into the most inner sheath, the actuator may be further actuated in a reverse manner, causing the telescoping inner sheaths to be retracted into one another, and into the interior volume of the outer sheath. Once retracted, the device may be removed from the sample collection site without contaminating or diluting, the collected specimen during the device's withdrawal.

Specimen-collection devices disclosed herein need not be of a single defined shape or dimension; rather, the specific shape and/or dimensions of embodiments of such devices may vary in accordance with the specimen to be collected and/or the environment of the specimen to be collected.

Having embodiments of the disclosed specimen-collection device available in a variety of sizes allows for increased comfort. Multiple sizes allow for an individual or their physician or health care provider to use the device with the most appropriate dimensions depending on the body cavity from which the specimen is to be collected and/or the individual's height, weight, number of vaginal deliveries, sexual experience, and/or other factors affecting comfort. An individual would be more likely to use a specimen-collection device configured for self-collection when empowered with multiple size choices for comfort and to avoid injury. Furthermore, a properly-sized specimen-collection device would reduce the likelihood of contamination of the specimen.

Embodiments of the present disclosure may include additional structures for identifying, recording, and transmitting information related to the specimen-collection device's use. These structures may include, but are not limited to, circuits, including timing circuit(s), location sensing circuit(s), and/or security circuit(s). Additionally, embodiments may provide for a processor and memory in communication with the aforementioned circuit(s), which may be configured to record information related to the specimen-collection device.

A security circuit may be configured to monitor and/or regulate access to, or modification of, any information stored in the memory (e.g. a dielet).

The security circuit may enable each specimen-collection device to be uniquely identifiable, and more specifically uniquely identifiable in a manner that comports to FDA UDI regulations. By enabling each individual specimen-collection device to be uniquely identified and monitored the security circuit may allow for CoC initiation and corroboration, while additionally facilitating inventory control, and CPT coding.

Inventory control may be achieved by having a database monitor the uniquely identified specimen-collection devices and notify appropriate personnel or an inventory management system, when the number of such devices in inventory falls below a predetermined number. Alternatively, the database may be configured to automatically order additional devices when it detects that the number of devices in inventory has fallen below a predetermined threshold.

The security circuit may facilitate the specimen-collection devices' conformity with FDA UDI regulations. These regulations imposed by the FDA mandate that medical devices have a means for UDI. FDA UDI regulations are set forth in Unique Device Identification System, 78 Fed. Reg. 58785 (Sep. 24, 2013) which is hereby incorporated by reference in its entirety. The same security circuit that may enable identification and tracking of each of these specimen-collection devices may be configured to enable the device to conform to FDA medical device UDI regulations.

Descriptions of certain illustrative aspects are described herein in connection with the annexed FIGURES. These aspects are indicative of various non-limiting ways in which the disclosed subject matter may be utilized, all of which are intended to be within the scope of the disclosed subject matter. Other advantages, emerging properties, and features will become apparent from the following detailed disclosure when considered in conjunction with the associated FIGURES that are also within the scope of the disclosure.

BRIEF DESCRIPTION OF THE DRAWINGS

The disclosed subject matter itself, as well as a preferred mode of use, further objectives, and advantages thereof, will best be illustrated by reference to the following detailed description of embodiments of the device read in conjunction with the accompanying FIGURES, wherein:

FIG. 15 depicts an example of a number of options for CPT coding a selection of different potential uses for different embodiments of the specimen-collection device.

FIGS. 19A-B depict an exemplary specimen collection site, specifically the space underneath a fingernail or toenail.

DETAILED DESCRIPTION OF ILLUSTRATIVE EMBODIMENTS

Reference now should be made to the FIGURES in which the same reference numbers are used throughout the multiple FIGURES to designate the same components.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

While the examples discussed in this disclosure relate mainly to the observation, collection, storage, handling, transportation, analysis, and preservation of biologic specimens, this is in no way intended to limit the teachings of this disclosure to such applications. It will be apparent to those skilled in the art that the embodiments of the device and the methods of its use as taught herein may be applied to any number of different scenarios related to specimen collection and preservation.

Figure 1:
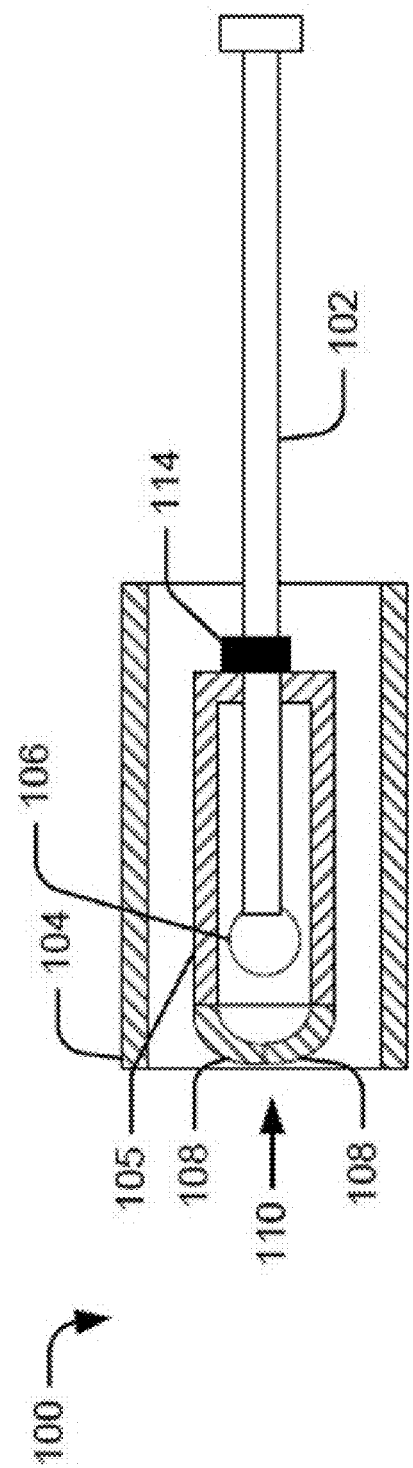
FIG. 1 depicts a cross-sectional view of a specimen-collection device in a closed configuration.

FIG. 1 illustrates a specimen-collection device. The specimen-collection device 100 of the embodiment depicted in FIG. 1 is in a closed configuration. Specimen-collection device 100 includes an actuator 102, an outer sheath 104, an inner sheath 105, a specimen collector 106, a cap 108, an actuation mechanism 114, and a seal 110. The actuator 102 is coupled to the specimen collector 106 and moves it between an extended position in which it is positioned outside of and extending from the inner 104 and outer 105 sheaths and a retracted position in which it is positioned within the sheaths 104 and 105. This movement of the inner sheath 105 through the motion of the actuator 102 is facilitated by actuation mechanism 114. Inner sheath 105 comprises a hollow cylinder of a length sufficient to contain the specimen collector 106 therein. Specimen collector 106 is coupled to the distal end of actuator 102. As actuator 102 is actuated, actuation mechanism 114 engages inner sheath 105 and urges it to extend from inside of outer sheath 104. As actuator 102 is actuated further (or actuated in an alternate manner), after inner sheath 105 reaches its extended configuration, actuation mechanism 114 engages cap 108 and causes cap 108 to open, allowing for specimen collector 106 to extend, unhindered, out from inner sheath 105. Once specimen collector 106 is in its fully extended configuration, actuation mechanism 114 engages with, and may prevent further positive actuation of, actuator 102 (actuator 102 may still be actuated in a reverse manner so as to retract both specimen collector 106 and inner sheath 105).

Figure 2:
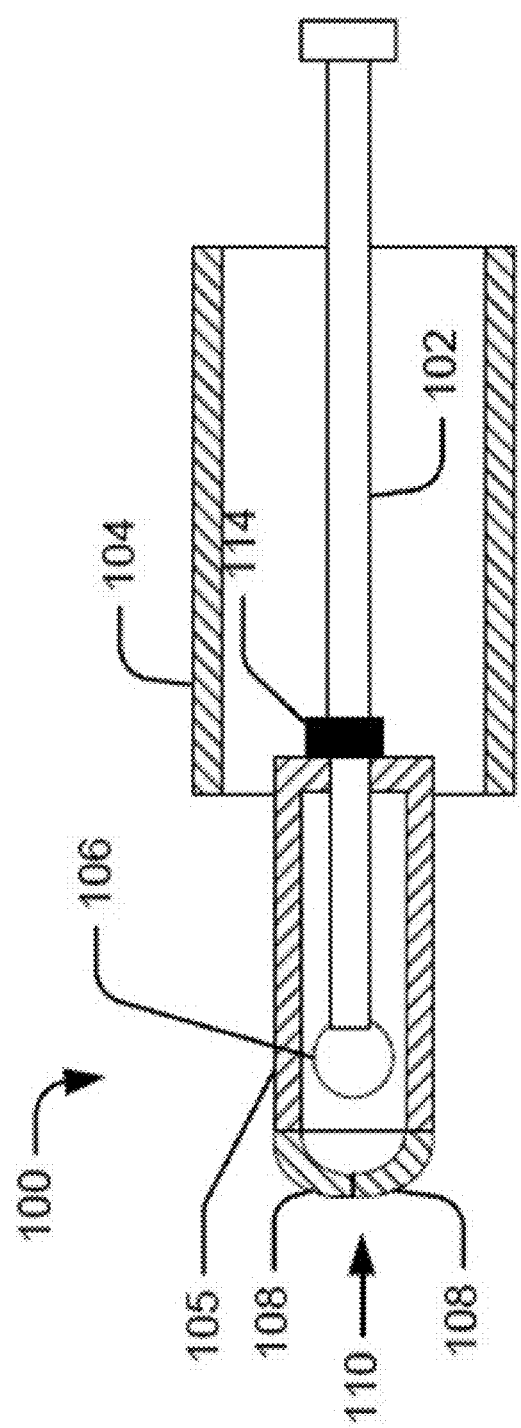
FIG. 2 depicts a cross-sectional view of a specimen-collection device in a partially open configuration, wherein a portion of an inner sheath has extended outside of the outer sheath in a telescoping fashion, but remains closed.

FIG. 2 depicts a cross-sectional view of a specimen-collection device 100 in a partially open configuration. The actuator 102 has been partially actuated (or partially actuated in the reverse direction from being fully actuated) causing a portion of inner sheath 105 to extend outside of outer sheath 104 in a telescoping fashion, while the specimen collector 106 is retained inside of the sealed inner sheath 105.

Figure 3:
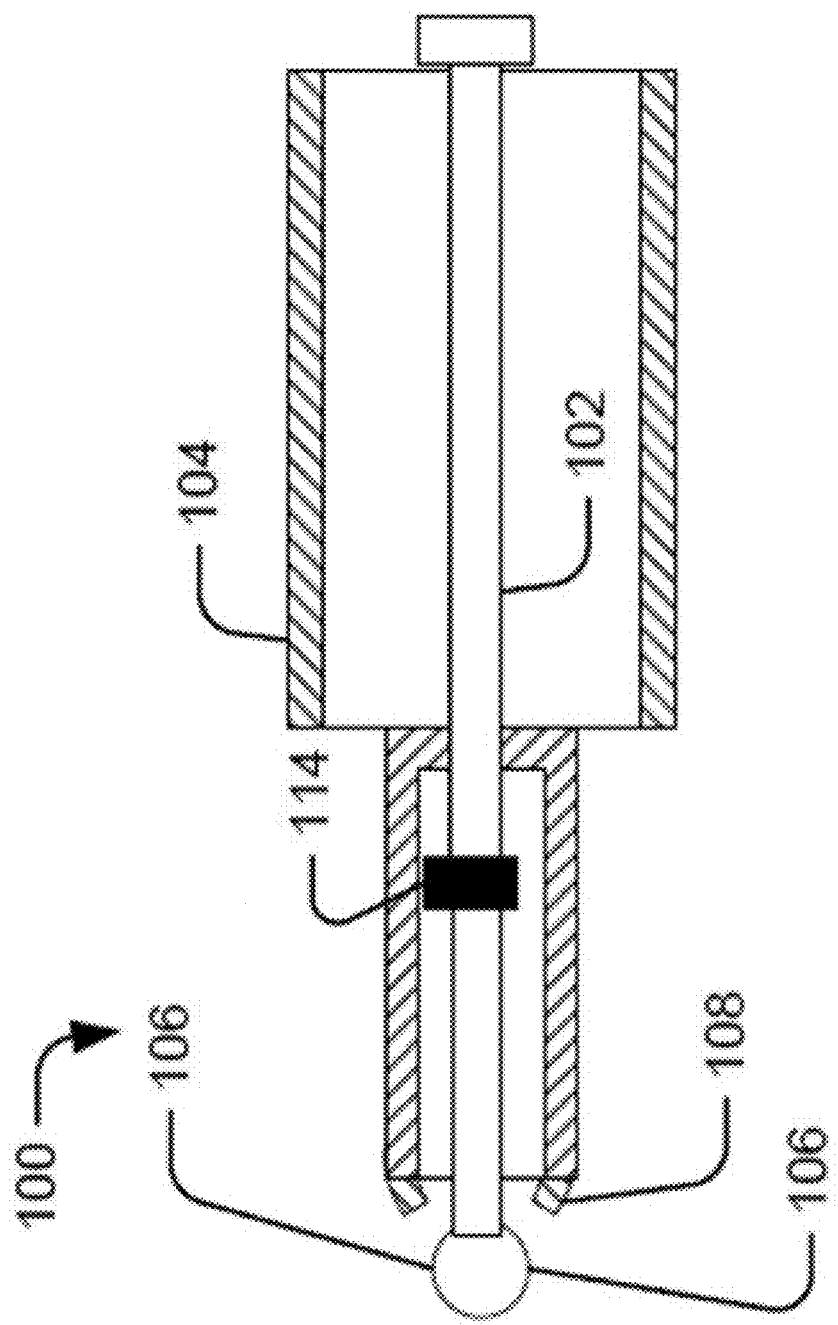
FIG. 3 depicts a cross-sectional view of a specimen-collection device in a fully open configuration wherein a portion of an inner sheath has extended outside of the outer sheath and is open and unsealed, and where the specimen collector is extended, exposed, and ready to receive a specimen.

FIG. 3 depicts a specimen-collection device 100 in a fully open configuration. The actuator 102 has been fully actuated, causing a portion of the inner sheath 105 to extend outside of the outer sheath 104 in a telescoping fashion, and further causing actuation mechanism 114 to open cap 108 and allow for the specimen collector 106 to extend outside of the inner sheath 105 in a telescoping fashion and to become exposed to the volume exterior to the specimen-collection device 100.

Figure 4:
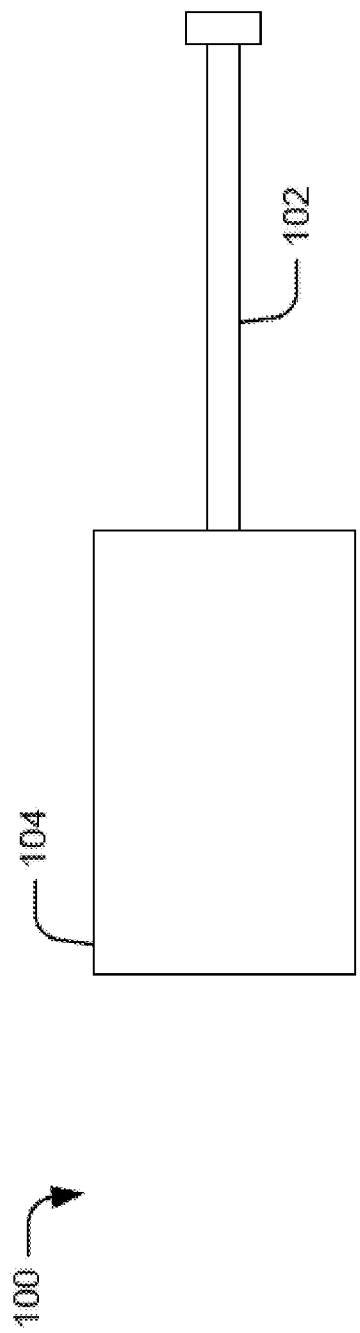
FIG. 4 depicts an exterior view of a specimen-collection device when in a closed configuration.

FIG. 4 depicts an exterior view of a specimen-collection device 100 in a closed configuration. In this depiction, the actuator 102 is in a fully un-actuated (or fully actuated in reverse) position causing all other parts of the specimen-collection device 100 to be retained coaxially within the exterior sheath 104.

In none embodiment, outer sheath 104 may be about 1 inch in external diameter and about 4 inches in length. Outer sheath 104 of this size should allow for comfortable insertion into a body cavity (e.g. vagina, anus, or mouth) of interest of most users. Devices provided by alternate embodiments of the disclosed subject matter could be adopted for insertion into other environments, including, but not limited to, alternate bodily cavities such as those exposed during surgery, requiring adjustments in diameter and length to accommodate the use and function of the procedure. In certain embodiments the specimen collector 106 may be approximately 4 to about 5 inches in length while the actuator 102 may be approximately 4 inches in length. As previously noted, the various dimensions of the device may vary in proportion to one another and may differ depending on the specimen being collected and the environment in which it is located.

Embodiments of the devices disclosed herein may include, but are not limited to, having an actuator ranging between approximately 2 and 8 inches in length and a specimen collector of approximately 4 inches in length. Other embodiments may provide for specimen-collection devices, wherein the diameter of the exterior sheath may be as small as mere fractions of an inch to approximately 3-4 inches.

Embodiments of the specimen-collection device of various shapes and dimensions may be used in lieu of, or in addition to, vaginoscope(s), anoscope(s), oral scope(s), otoscope(s), nasoscope(s), laproscope(s), speculum(s), obturator(s), or other instruments.

FIG. 2 illustrates a specimen-collection device 100 in a partially open configuration. In the partially open configuration depicted the actuator 102 has been partially actuated causing a portion of the inner sheath 105 to extend from the outer sheath 104 in a telescoping fashion. However, the actuator 102 has not been actuated to the point where actuation mechanism 114 has caused cap 108 to open (which in turn would breach seal 110), thereby maintaining specimen collector 106 inside of the sealed inner sheath 105.

The configuration of the specimen-collection device 100 depicted in FIG. 2 allows for the specimen collector 106 to be inserted deeply into a body cavity (or other environment) before being removed from the sealed interior of the inner sheath 105. This facilitates contaminant-free, non-diluted collection of specimens from such environments by allowing the specimen collector 106 to only become exposed to an environment exterior to the sealed interior of inner sheath 105 when it is in proximity with the specimen collection site.

FIG. 3 depicts a specimen-collection device 100 in a fully open configuration. In this fully open configuration the actuator 102 has been fully actuated, causing actuation mechanism 114 to cause a portion of inner sheath 105 to extend outside of outer sheath 104 in a telescoping fashion and causing actuation mechanism 114 to cause specimen collector 106 to traverse the cap 108 and seal 110 and extend from the inner sheath 105 in a telescoping fashion, becoming exposed to the volume exterior to specimen-collection device 100. The fully open configuration of the specimen-collection device 100 illustrated in FIG. 3 allows for specimen collector 106 to become exposed in order to facilitate the collection of a specimen.

FIG. 4 depicts an exterior view of specimen-collection device 100 in its closed configuration, wherein actuator 102 is in its fully un-actuated (or full actuated in the reverse) state and all parts of specimen-collection device 100 except for said actuator 102 are retained inside of outer sheath 104.

Figure 5:
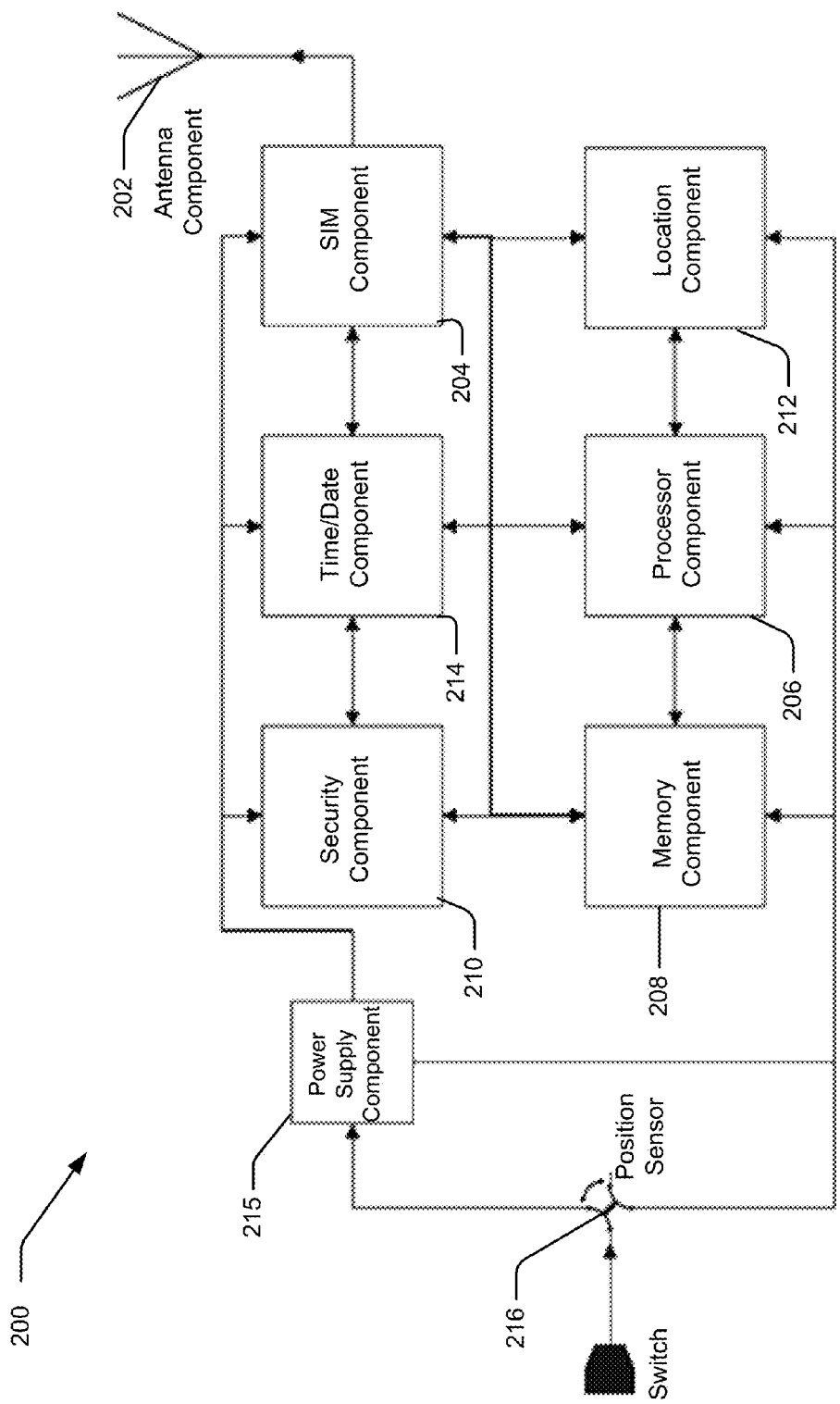
FIG. 5 depicts an exemplary circuit diagram of a circuit capable of identifying, recording, and transmitting information, including but not limited to a date, time, and location (DTL) in a date, time, and location stamp (DTLS), which may be incorporated into embodiments of the specimen-collection device, and/or its packaging.
Figure 6:
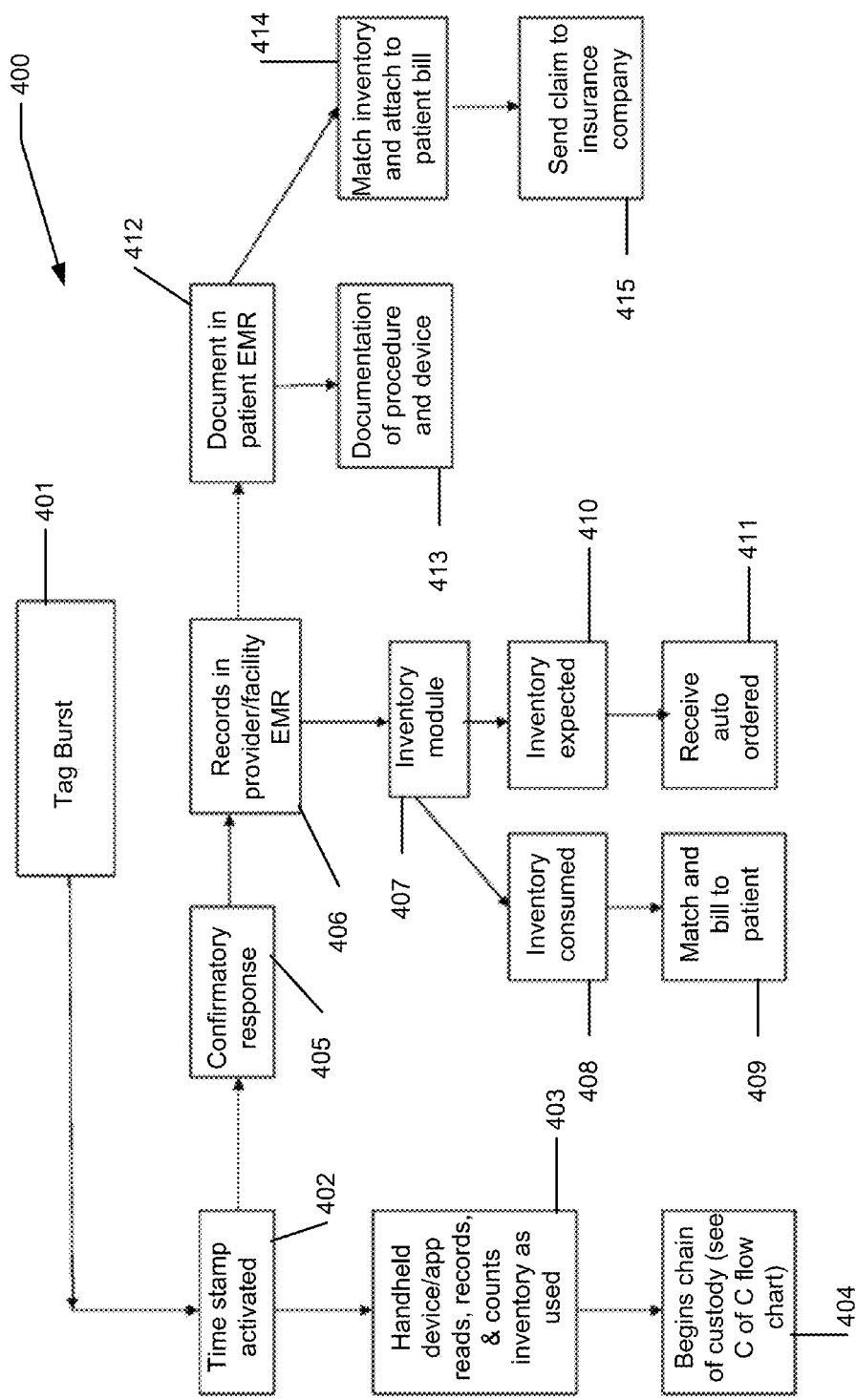
FIG. 6 depicts a flowchart exemplifying a manner in which the circuit provided for in embodiments of specimen-collection device may identify, record, and transmit information related to the specimen-collection device, and how that information may be used for CoC, CPT coding, and inventory control purposes.
Figure 7A:
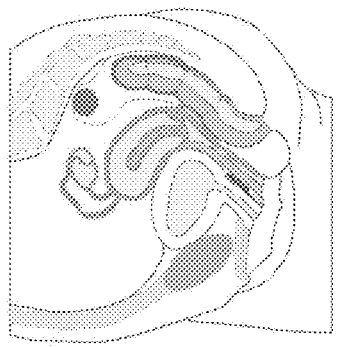
FIGS. 7A-F depict exemplary specimen collection sites, specifically cross-sectional views of various human body cavities.
Figure 7B:
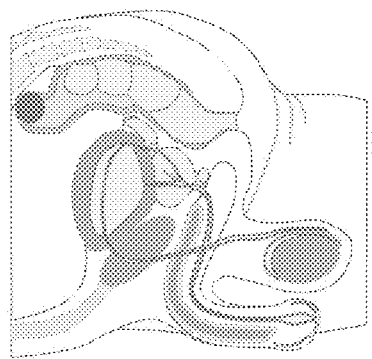
Figure 7C:
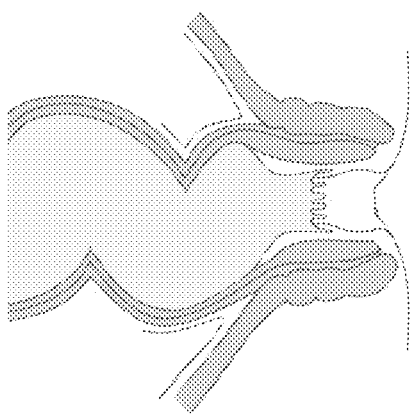
Figure 7D:
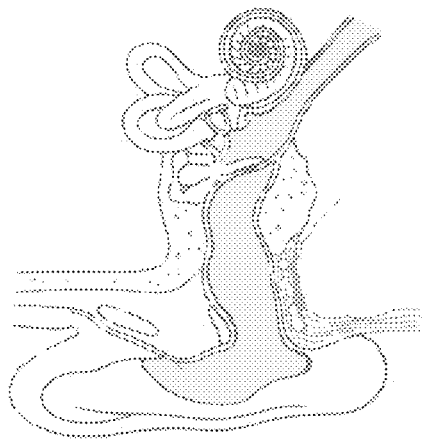
Figure 7E:
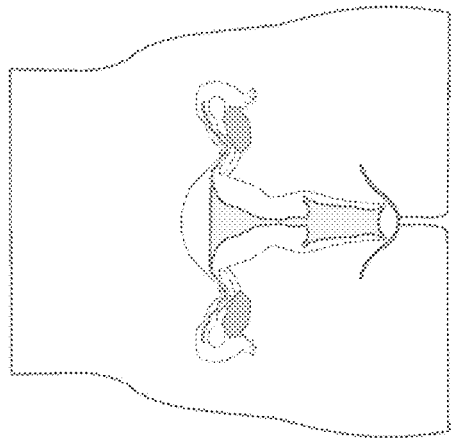
Figure 7F:
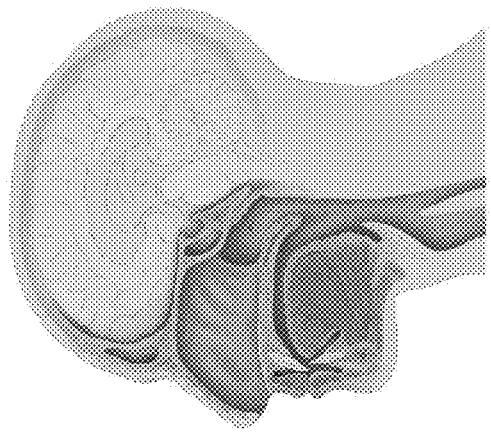

FIG. 5 illustrates a schematic diagram of an exemplary circuit which may be provided for in embodiments of the specimen-collection device. More specifically, FIG. 5 illustrates a circuit 200 including an antenna 202, a subscriber interface module (SIM) component 204, a processor 206, a memory 208, a security component 210, a location component 212, a time (and/or date) component 214, a power component 215, and a switch 216. Most of the components of the circuit 200 communicate electronically with the processor 206 either directly or indirectly, while the various components 210, 212, and/or 214 reside on, execute on, etc. the processor component 206. More specifically, the switch 216 communicates with the processor component 206 for determining actions associated with the specimen-collection device's use.

Embodiments of the processor 206 may include any type of processor capable of executing various applications such as the time and/or date module 214, the location module 212, the security module 210, etc. An alternate embodiment may allow the processor modules to be implemented in the included hardware. The time and/or date module 214 may maintain a clock to record the time of day and a day, time, and year feature that may communicate via the SIM circuit 204 to send/receive information related to the time and/or date. For instance, the time and/or date module 214 may comprise a timer that relies on some external service/source for date information, time change information, etc. Additionally, the time and/or date module 214 may be configured to send to the memory 208 the current time and/or date whenever the switch 216 opens and/or closes. In this way, the present disclosure time/date stamps the action of the switch 216. The switch 216 may be activated by one or more of any number of actions, including but not limited to, the opening/closing of cap 108, the actuation of actuator 102, the opening the packing in which the specimen-collection device 100 is originally sealed, etc. The memory 208 may store a multi-entry table of such time stamped operations of the specimen-collection device 100.

In addition to or alternatively, FIG. 5 illustrates that the processor may execute the location module 212. More specifically, the location module 212 may be configured to determine the location of the specimen-collection device 100. Various location techniques may be employed by the location module 212 working in conjunction with the SIM card 204 and/or antenna 202. The location module 212 can determine its location via time-delayed receipt of signals from various in-range cellular base stations (i.e., antennas), Global Positioning System (GPS) based signals, etc. and derive the location or best approximation of the device's location therefrom. In some embodiments, the location module 212 may query external services/systems (such as cellular telephony systems) in order to determine its location or the nearest location that such services are available to provide. Additionally, the location module 212 may be configured to store its location information in the memory 208 when the switch 216 activates. Accordingly, the embodiment enables the location at which the specimen-collection device was operated to be stored in and recalled from the memory 208.

The time circuit(s) and location sensing circuit(s) may be configured to allow the memory of the device to record and store date, time, and location information related to the use of the device in a date/time/location stamp (DTLS). The DTLS comprises information related to the time, date, and location when/where the device was used. The DTLS may be used as evidence that may corroborate the validity of, and circumstances related to, or an account of the collection of a specimen. This generation of corroborating evidence is of particular importance in the event that a specimen is collected outside of the legal system's control (e.g. self collection or collection in a remote location).

In different embodiments the triggering of the time and location circuits in order to create a DTLS may be tied to the actuation of the device's actuator, to the opening of the device's cap, to the unsealing and/or sealing of the device's seal, or to the opening of the packaging in which the specimen-collection device is distributed to users, etc. The result of such a triggering of said circuits being an information burst in which the information associated with the specimen-collection device's use is identified and recorded.

FIG. 5 also depicts an exemplary circuit comprising a security module 210. The security module 210 may be configured to protect the information (the DTLS(s) for example) stored in the memory 208. The security module 210 may also provide security for the processor 206, so that malware and/or other attempts to fake, spoof, destroy, tamper with, etc. the information being generated by the processor 206 (or the modules executing thereon) or stored in the memory 208 may be prevented or alternatively readily detected. For example, access to the memory 208 and/or modules executing on the processor 206 may be password protected, encrypted, etc. by the security module 210. Some embodiments of the specimen-collection devices 100 may include some form of physical security (e.g. a dielet, or lock, etc.) for the circuit 200 by one or more techniques. For example, the circuit may be sealed inside a closed container or even embedded in protective material such that an attempt to physically alter, access, etc. the circuit 100 (and/or its components) may be prevented or alternatively, readily detected. Alternatively, or in addition, security module 210 may be configured to enable the specimen-collection device 100 to be uniquely identifiable.

The memory 208 may be any type of computer readable medium capable of storing the information obtained by the device including, but not limited to, DTLS(s) generated by various embodiments of circuits 200. For example, the memory 208 could be any type of non-volatile memory such as flash memory.

The SIM card 204 and the antenna 202 may be configured to function with particular types of telecommunications systems. For example, some embodiments may use Code Division Multiple Access (CDMA), SIM cards 204, and antennas 202 with associated protocols. Other embodiments may use Global System for Mobile communications (GSM), or radio frequency identification (RFID) compatible hardware with their respective associated protocols. Further embodiments may use other communication standards not listed in conjunction with the circuits integrated into the specimen-collection device in order to facilitate transmission of the collected information.

In one embodiment the means for uniquely identifying and/or DTL stamping a specimen-collection device may be through the use of RFID. In such an embodiment, the RFID component of the specimen-collection device may begin in a non-active state and then become active upon the triggering of the time and location circuits or the resultant generation of the information burst.

In some embodiments, the specimen-collection device may further comprise a transmitter, antenna, and/or other structures connected to the device's memory such that the memory may be configured to communicate with a network, including wireless and secure networks, in order to facilitate the transmission of information stored in the specimen-collection device's memory to remote devices. Such remote devices may include, but are not limited to, computers, mobile computing devices (e.g. smart phones, tablets, etc), databases (including secure databases), etc. These remote devices may be capable of generating and transmitting responses upon receipt of information, or upon being queried by an outside source (e.g. law enforcement agencies, laboratory facilities, etc.), in order to confirm the receipt of said information, or to confirm transfer of the specimen-collection device. The remote device may additionally record the identity of outside sources requesting or verifying said information for CoC purposes.

In some embodiments, the security or location circuit(s) that may allow for tracking the location of, and access to, the specimen-collection device in order to identify, establish, or corroborate, a CoC that may be independently verified. Such a security/location circuit configured to track the location of the device may additionally be used for inventory control purposes.

Figure 14:
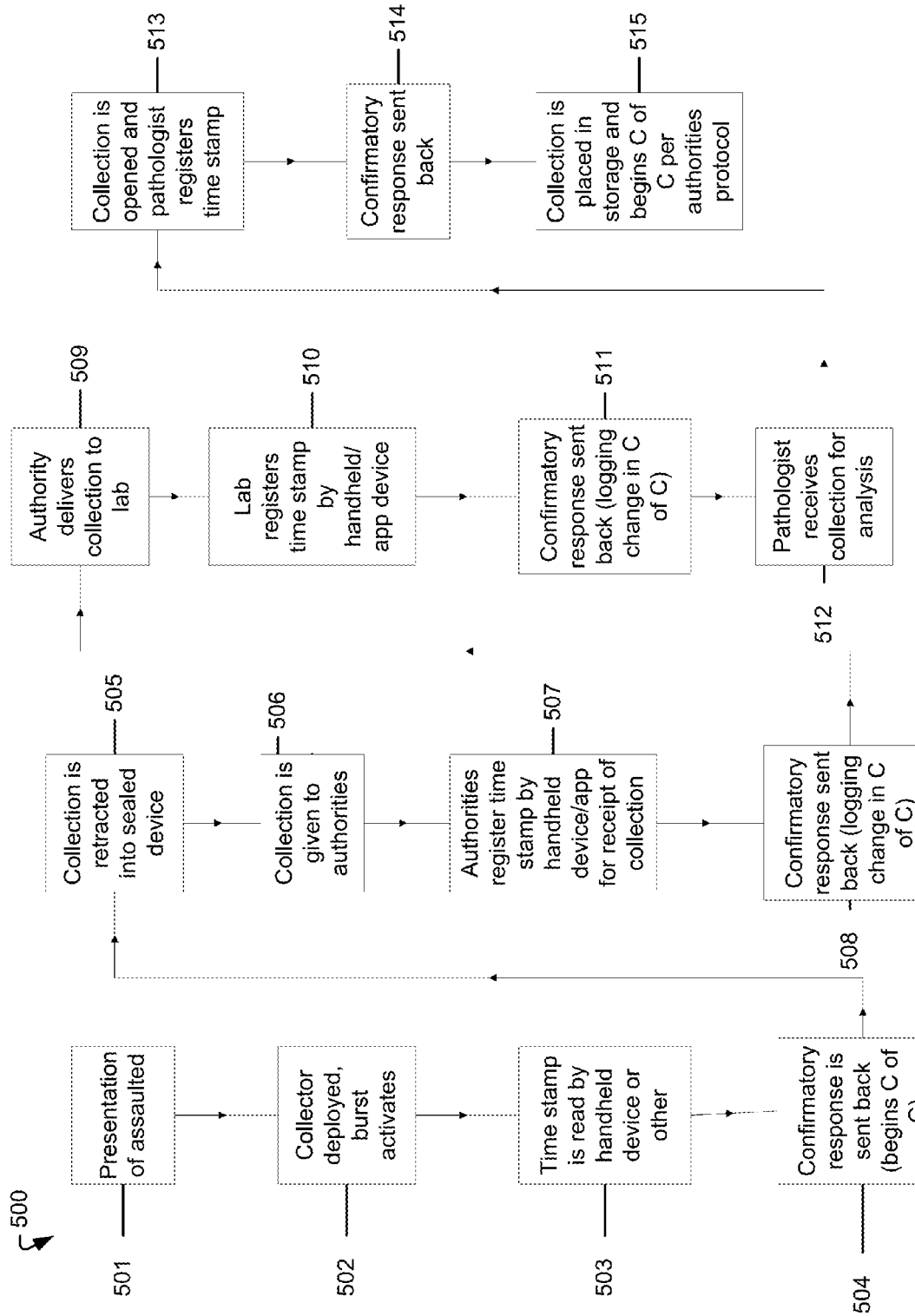
FIG. 14 depicts a flowchart detailing an exemplary process to establish an identifiable and verifiable CoC related to specimens collected using embodiments of the specimen-collection device.
Figure 16:
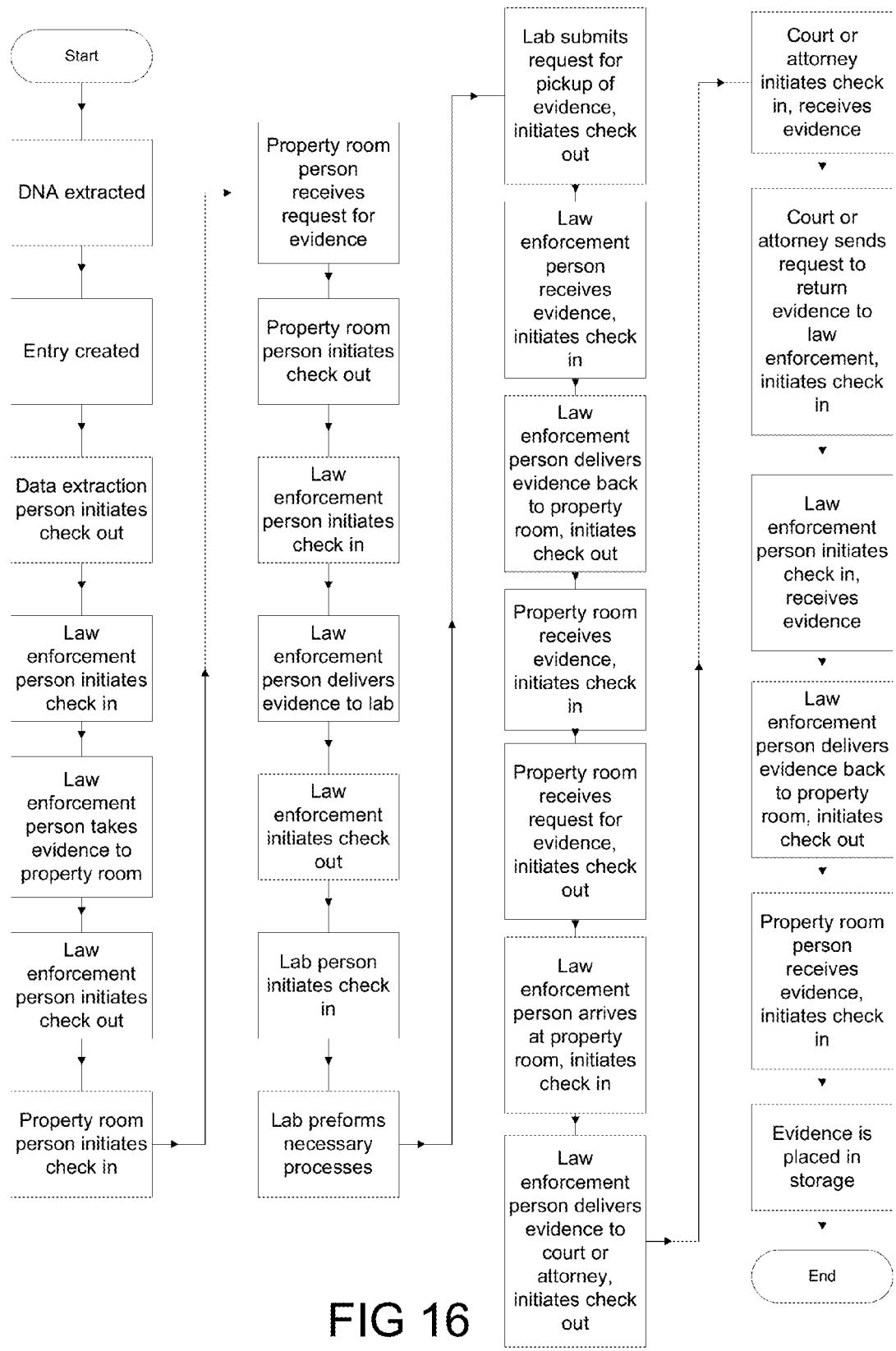
FIG. 16 depicts a flowchart detailing an exemplary method of creating a CoC for a specimen collected by a specimen-collection device and maintaining said CoC throughout the course of the evidence processing procedure.
Figure 17:
FIG. 17 depicts an exemplary specimen collection site, specifically the skin on the surface of an arm and/or hand.
Figure 18:
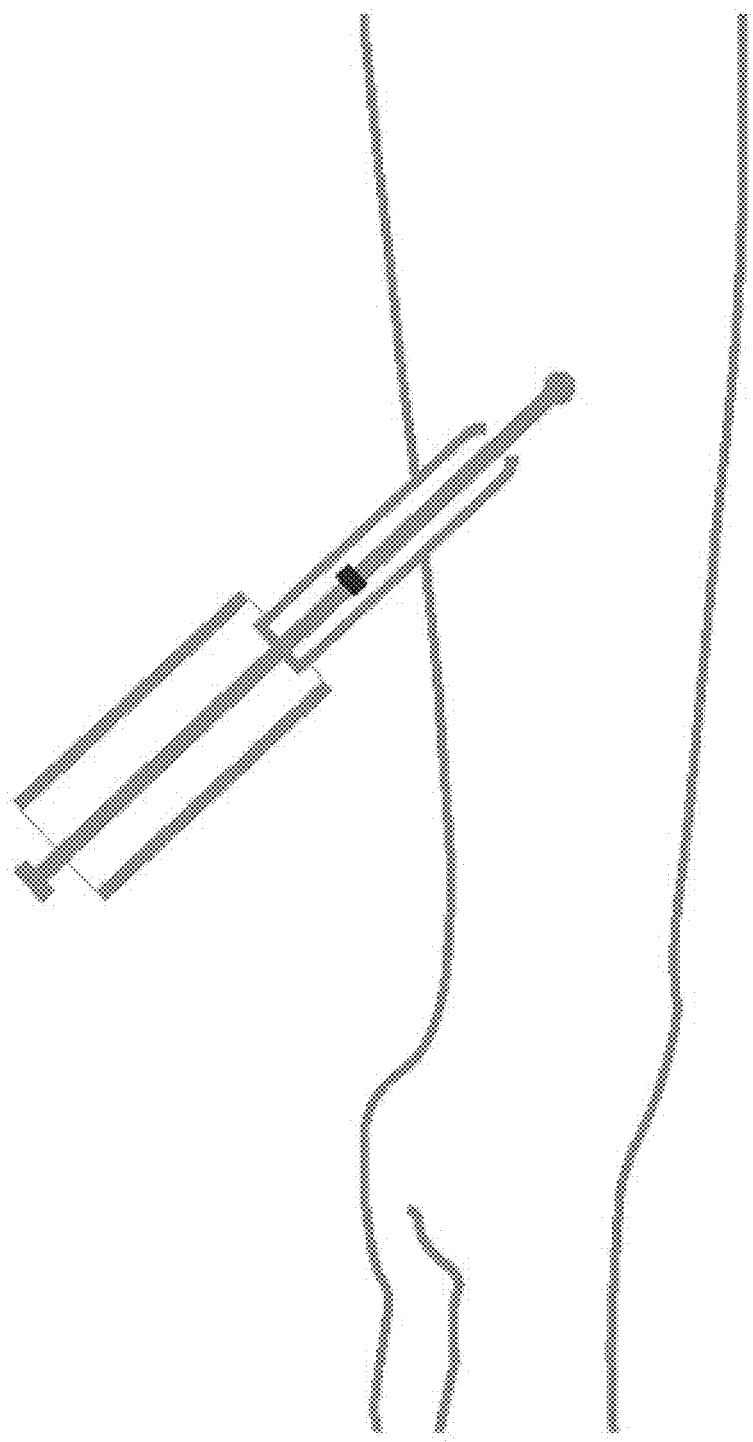
FIG. 18 depicts the use of a specimen-collection device for collecting a specimen from an exemplary specimen collection site, specifically from the surface of the skin.

FIG. 14 depicts a flowchart 500, exemplifying a set of steps that may be used to create, identify, and support a CoC for a specimen collected with a specimen-collection device, including the manner in which DTL stamping may be used to interact with and augment the CoC identification procedure. Flowchart 500 begins with step 501, in which the victim of sexual assault is presented. The victim of a sexual assault, or other assisting individual(s), then may use a specimen-collection device to collect a specimen to be used as evidence of the sexual assault, and in-so-doing triggers the circuit(s) to capture information associated with the collection in an information burst, as shown in step 502. The DTLS generated in the information burst may then be transmitted to, or read by, a remote device as in step 503. Step 504 shows that the remote device may then generate and return a confirmatory response indicating that it has received the information, thus beginning the CoC. The collected specimen may then be retracted into and, sealed inside of, the specimen-collection device in step 505. Then, in step 506, the specimen-collection device containing the collected specimen may then be transferred to the authorities. The authorities may then register the DTLS associated with the collection of the specimen through use of a remote device in accordance with step 507. The remote device may then send a further confirmatory response, and log the change in the CoC as indicated in step 508. This logging of the DTLS associated with the collection of the specimen, and the remote devices' sending of a confirmatory response and logging of the change in the CoC is then repeated each time possession of the specimen-collection device, and the collected specimen retained inside of the specimen-collection device, is transferred (steps 509-515).

FIG. 15 depicts an exemplary method in which embodiments of the specimen-collection device may be configured so that the electrical circuits integrated into the device may identify and/or indicate the CPT coding related to the devices use. This integrated CPT coding identification and association with the device may provide a simpler and less error-prone means of CPT coding the device's use (for medical documentation and billing purposes) than what is currently known in the art.

Figure 8:
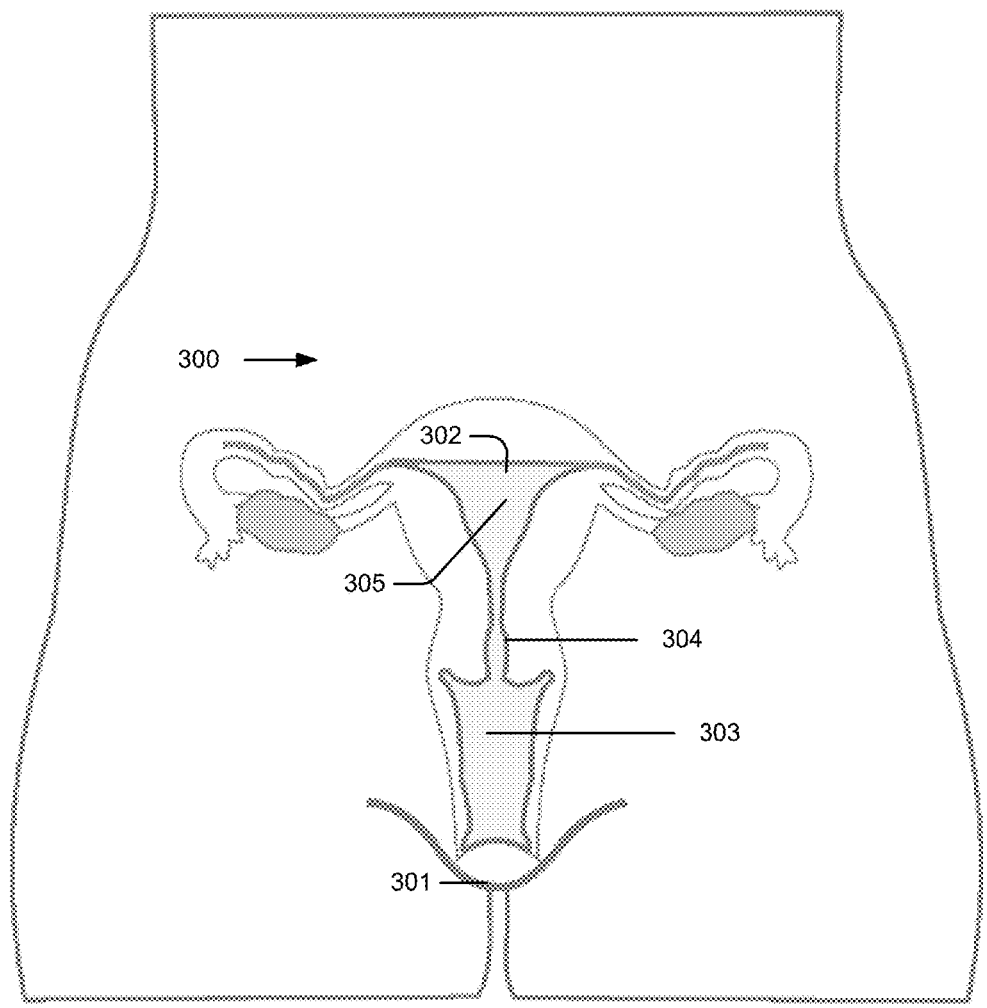
FIG. 8 depicts an exemplary specimen collection site, specifically body having a cross-sectional view of a female reproductive system.

FIG. 8 depicts an exemplary specimen collection environment, in this case a body 300 having a body cavity (and more specifically a vaginal cavity). Here, body 300 has a vaginal opening 301, which provides access from the outside of the body 300 to the vagina 303, and a specimen collection site 302 located inside of the uterus 305, which is beyond the cervix 304.

Figure 9:
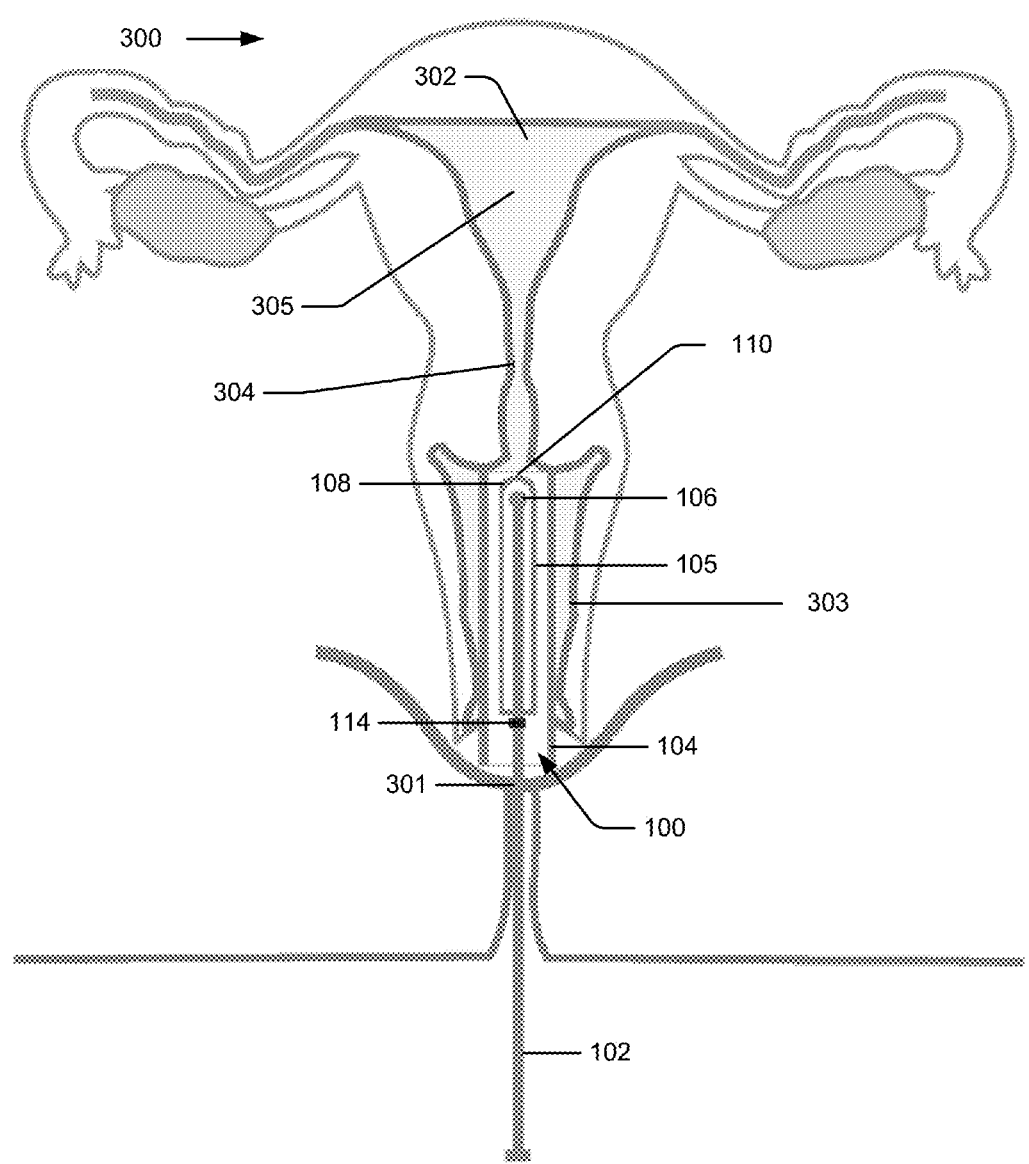
FIG. 9 depicts a cross-sectional view of a specimen-collection device inside of a vaginal body cavity while the specimen-collection device is in its initial closed and sealed configuration.

FIG. 9 depicts a specimen-collection device 100 in an initial closed configuration retained within the vagina 303 having been inserted through the vaginal opening 301.

Figure 10:
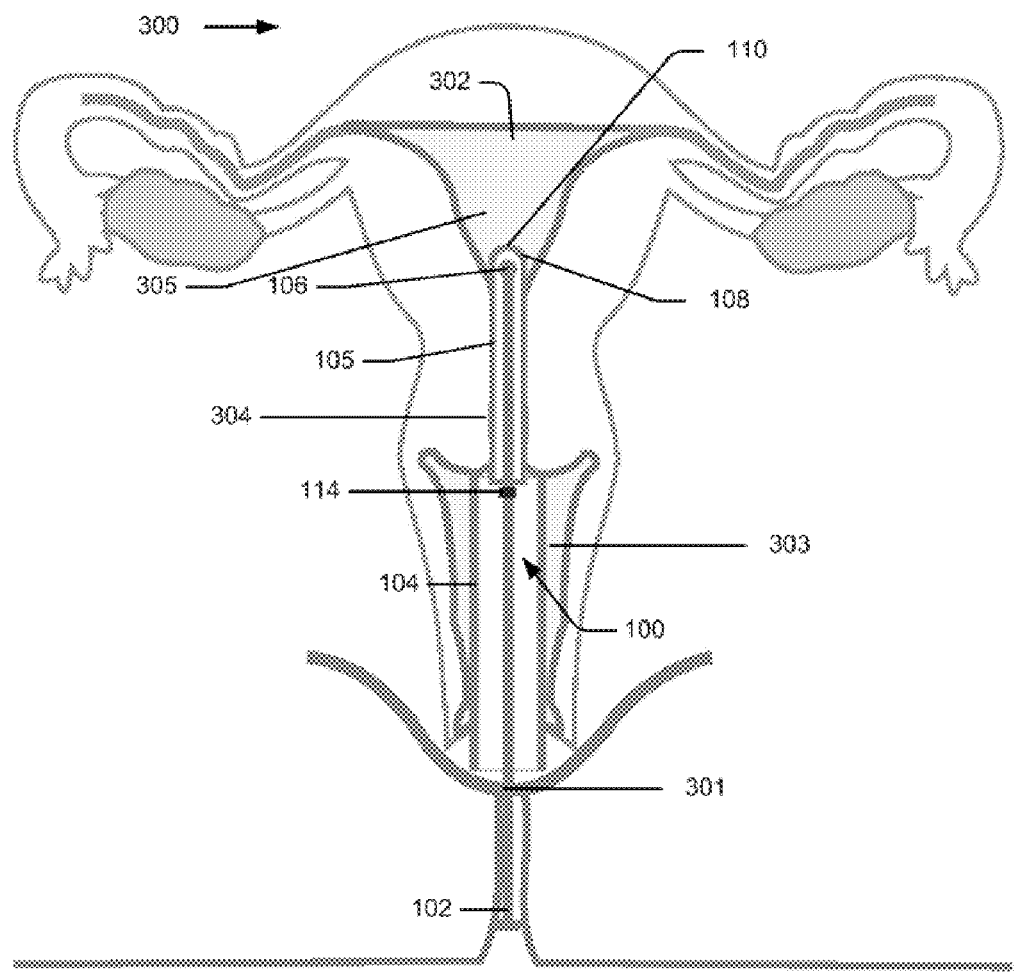
FIG. 10 depicts a cross-sectional view of a specimen-collection device inside of a vaginal body cavity wherein the specimen-collection device has been partially actuated and is in its partially open configuration.

FIG. 10 depicts a specimen-collection device 100 in an intermediary, partially open, configuration within the body 300. The actuator 102 has been partially actuated causing a portion of inner sheath 105 to extend outside of outer sheath 104 in a telescoping fashion, wherein inner sheath 105 has extended past the cervix 304, nearing specimen collection site 302, while the outer sheath 104 remains in the vagina 303.

Figure 11:
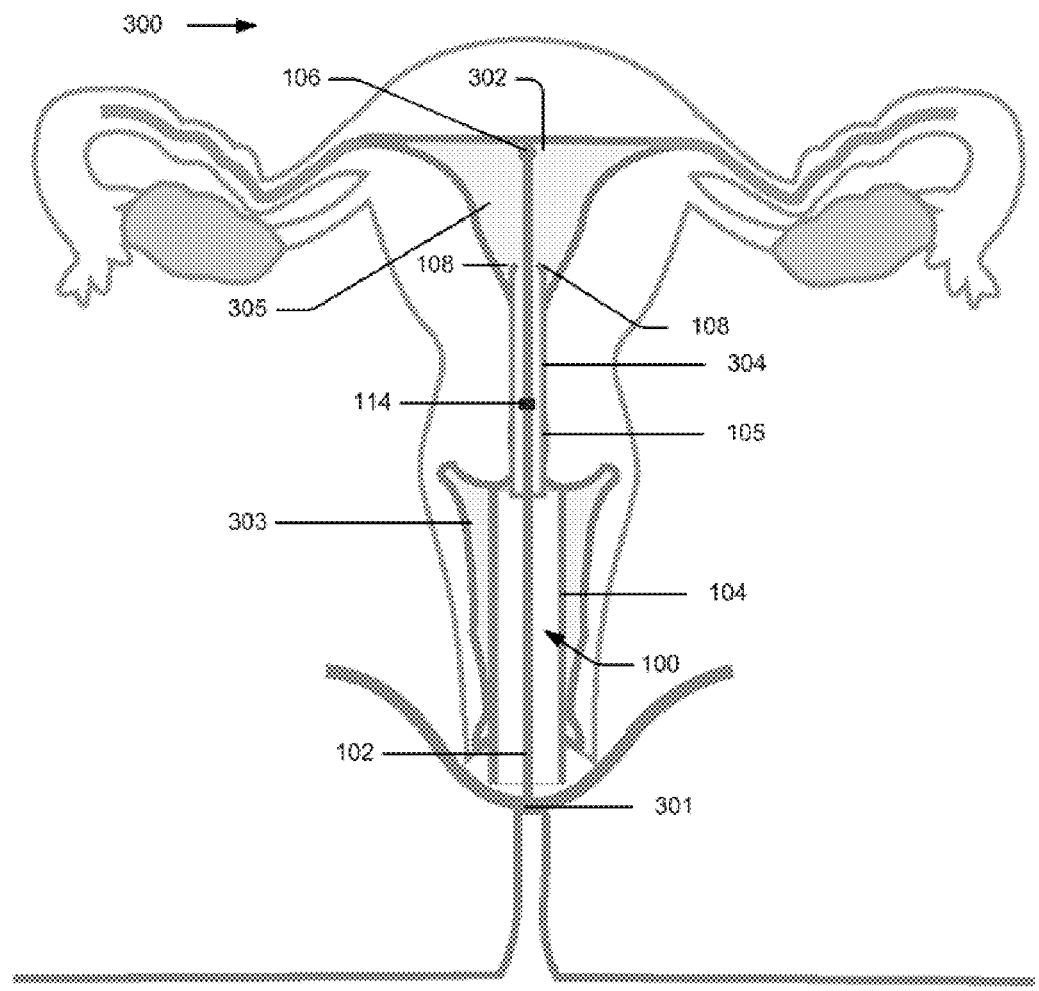
FIG. 11 depicts a cross-sectional view of a specimen-collection device inside of a vaginal body cavity wherein the specimen-collection device is in its fully open configuration having an exposed specimen collector in proximity to the specimen collection site.

FIG. 11 a specimen-collection device 100 in a fully open configuration while inside of a body 300. The actuator 102 has been fully actuated causing a portion of the inner sheath 105 to extend outside of the outer sheath 104 in a telescoping fashion, and further causing the specimen collector 106 to traverse the cap 108 and extend outside of the inner sheath 105 in a telescoping fashion. In this configuration the specimen collector 106 is in an exposed position proximate to the specimen collection site 302, while the inner sheath 105 remains mostly inside of the cervix 304 and the outer sheath 104 remains inside of the vagina 303. The complete actuation of the actuator 102 and the resultant exposure of the specimen collector 106 while in proximity to the specimen collection site 302 allows the specimen collector 106 to collect a specimen from specimen collection site 302.

Figure 12:
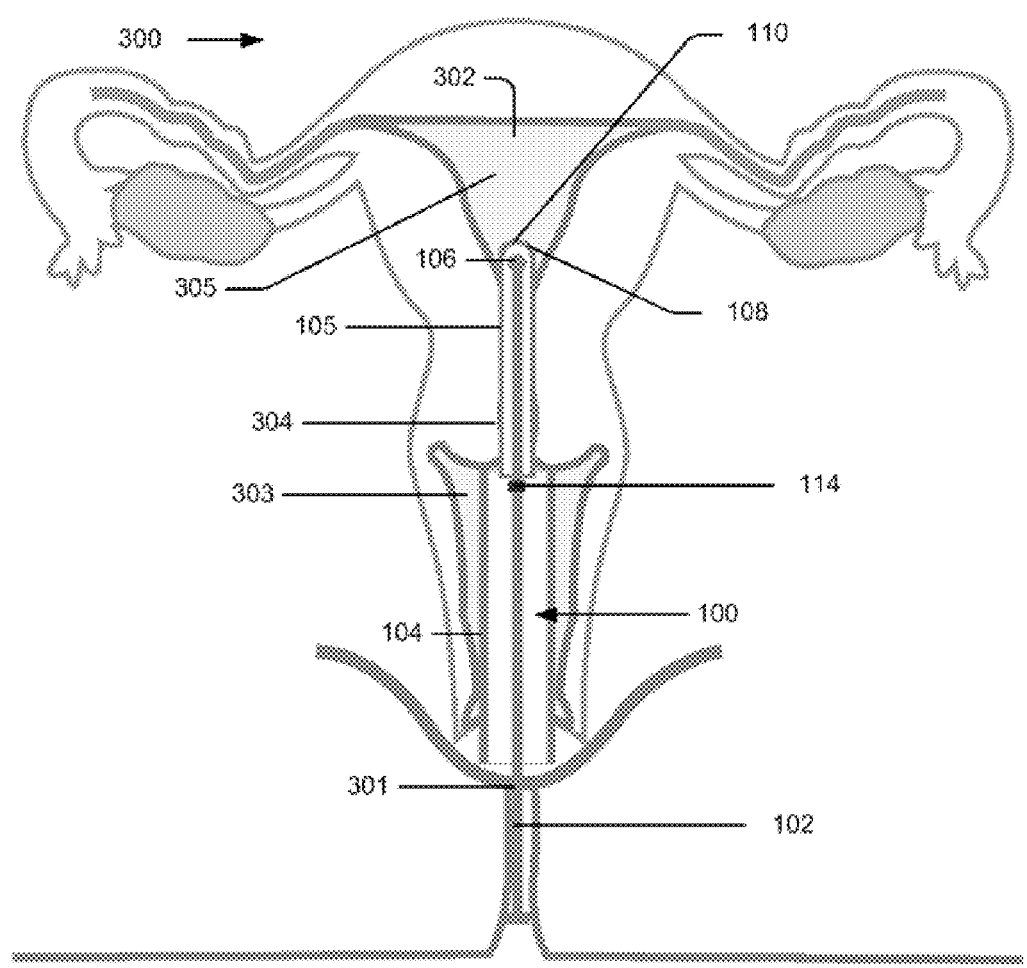
FIG. 12 depicts a cross-sectional view of a specimen-collection device inside of a vaginal body cavity wherein the specimen-collection device has been partially actuated in reverse from its fully open configuration and has returned to its partially open configuration, wherein the specimen collector has been retracted into, and sealed inside of, the inner sheath.

FIG. 12 depicts a specimen-collection device 100 in a partially retracted, partially open, configuration while inside of a body 300. Here, the specimen has already been collected by the specimen collector 106 from the specimen collection site 302. After having collected the specimen, the actuator 102 has been actuated partially in the reverse direction, causing the specimen collector 106 to disengage from its interaction with the specimen collection site 302 and return to the interior of inner sheath 105. Once the specimen collector 106 has entered into the interior volume of the inner sheath 105 the actuation mechanism 114 causes the cap 108 to close and the seal 110 to seal the interior of inner sheath 105 from the volume exterior to specimen-collection device 100. This allows for further retraction of the specimen-collection device 100 from inside of the body 300 while preventing the specimen collector 106 from becoming exposed to any sites other than the specimen collection site 302, thereby preventing the possibility of specimen contamination or dilution from other areas of the body 300 during its retraction and removal.

Figure 13:
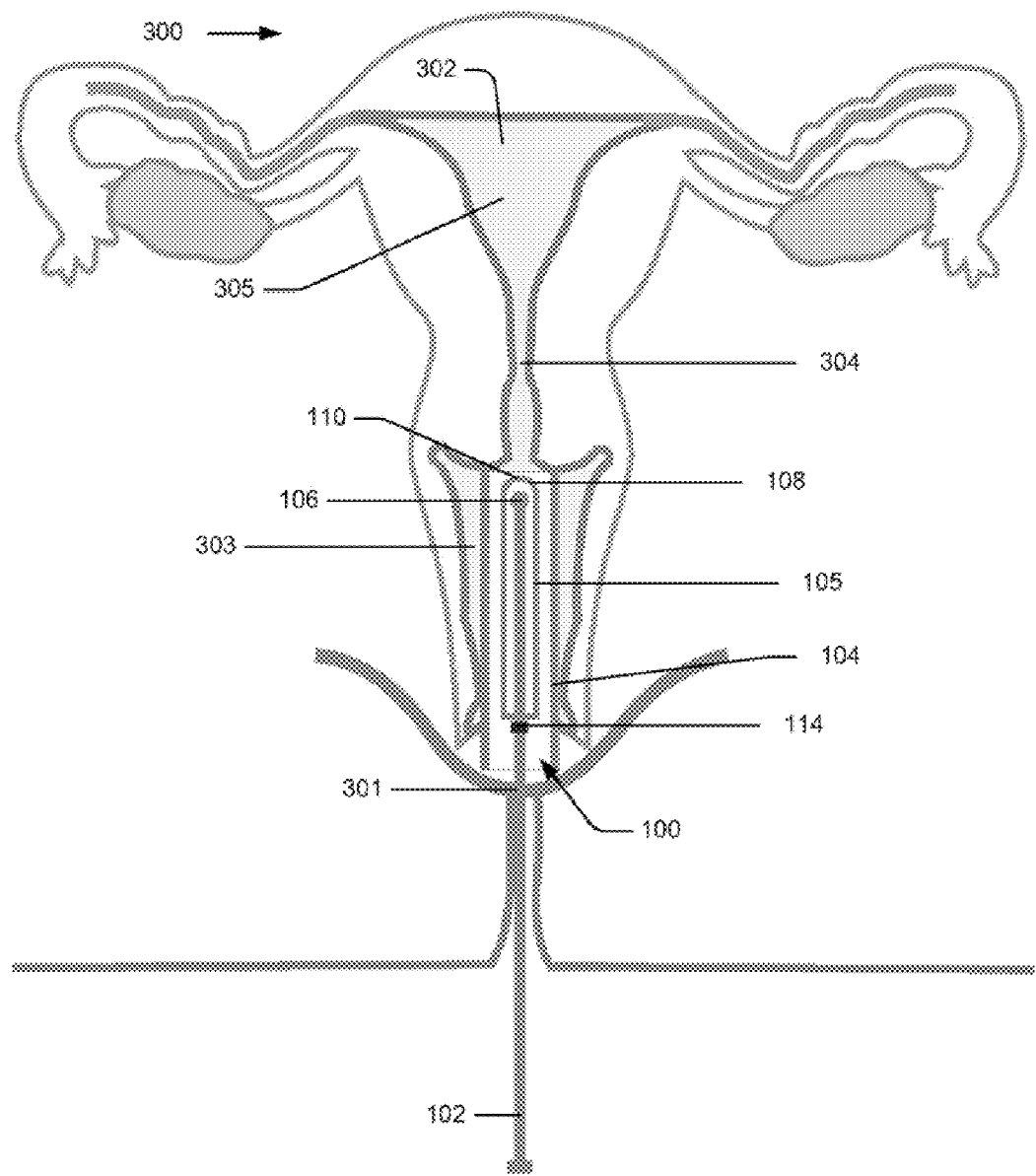
FIG. 13 depicts a cross-sectional view of a specimen-collection device inside of a vaginal body cavity wherein the specimen-collection device has been fully actuated in reverse and has returned to its fully closed and sealed configuration.

FIG. 13 depicts a specimen-collection device 100 in a fully retracted, closed, configuration while inside of a body 300. Here, the specimen has already been collected by the specimen collector 106 from the specimen collection site 302. After having collected the specimen, the actuator 102 has been fully actuated in the reverse direction, causing the specimen collector 106 to disengage from its interaction with the specimen collection site 302 and return to the interior of inner sheath 105, further causing the inner sheath 105 to return to the interior of the outer sheath 104. The specimen-collection device 100 is now in a closed and sealed configuration and is ready for removal from the body 300 through the vaginal opening 301.

Some embodiments of the specimen-collection device may be configured to allow a user to collect specimens from their own body without assistance (self-collection). Alternatively, the user of the specimen-collection device 100 may be an individual (e.g. a trained health care professional or an untrained individual) other than the victim of a sexual assault. Additionally, the specimen-collection device 100 may be used for purposes other than DNA evidence collection (e.g. pap spear sampling, human papillomavirus (HPV) sampling, and medicine delivery). For instance, the device may be used to obtain other forms of evidence from a crime scene or specimens not constituting DNA evidence from any location of interest.

In some embodiments, the actuator portion of the specimen-collection device may be a rod with a handle located at the proximal end of the device with the specimen collector being located at the distal end of the specimen-collection device. Other embodiments may have alternate devices, attachments, tool, and/or accessories at the distal end of the actuator, in place of the specimen collector.

In one embodiment, the actuator operably couples with the specimen collector and the inner sheath through the use of one or more actuation mechanisms, and may be adapted to move the specimen collector longitudinally relative to the sheaths. Accordingly, as the actuator is operated, the specimen collector may move between a retracted position and an extended position relative to the sheaths.

In an embodiment, the specimen collector portion of the specimen-collection device may be exposed by actuating the actuator portion of the device completely. In other embodiments, the specimen collector portion of the device may only be exposed by an alternate method of actuating the actuator, whereby the primary method of actuation causes the extension and retraction of the devices' inner sheath(s) and the alternate method of actuation (e.g. rotation of the actuator) cause the extension and retraction of the specimen collector.

The specimen collector 106 may be a cotton swab or any other type of specimen collector suitable for insertion into the appropriate body cavity or other specimen collection site. Specimen collectors other than cotton swabs may also be used with the specimen-collection device 100. Any material, device, etc. that can collect a specimen may be used as the specimen collector 106. For example, a brush or appropriately sized roller (similar to an appropriately sized lint roller) may be used as the specimen collector 106. In some embodiments, adhesive tape may cover the specimen collector 106 so that anything that comes into contact with the specimen collector 106 will adhere to it. Additionally, the specimen collector 106 need not be limited to just configurations that solely retrieve the sought-after material. For example, the specimen collector 106 may include indicator chemicals, reagents, or other materials, such as dyes used to detect human blood, animal blood, chemicals, certain other conditions (e.g. environmental pH levels, etc.) etc.

Alternatively, other devices, tools, attachments, and/or accessories may be coupled to the specimen-collection device 100 in the place of the specimen collector 106 so as to facilitate a multitude of functions. Examples of such devices, tools, attachments, and/or accessories include, but are not limited to, tweezers, brushes, silk, Dacron on paper, plastic sticks, scissors, spoons, punches, bores, needles, etc.

Some embodiments may provide quick attachment features to allow one end attachment (perhaps a specimen collector) to be replaced with another end attachment, such as a specimen collector of a different size, type, and/or configuration. Alternatively the quick attachment feature may facilitate the attachment of an applicator or some other type of end attachment device in the place of the specimen collector 106.

In an exemplary method of the disclosed device's use, the user starts with the specimen collector 106 in its retracted position within the inner and outer sheaths 104 and 105. The user may then insert the distal end of the outer sheath 104 into the body cavity of interest, such as the body cavities shown in FIGS. 7A-F, (or other specimen collection location) to a depth of approximately 4 inches such that the rim of the sheath 104 comes to rest proximal to the body cavity or the surface of the user's body. The rim (and/or end) of the outer sheath 104 may present a slightly raised surface relative to the rest of the outer sheath 104 such that the raised surface of the rim provides the user an indication of how far to insert the specimen-collection device 100 into the body cavity. Once the specimen-collection device 100 has been inserted into the body cavity to a desired depth, the user may then actuate the actuator 102 thereby causing the specimen collector 106 to move further into the body cavity and to expose the specimen collector 106. The user may then operate the actuator 102 in reverse in order to retract the specimen collector 106 into the inner sheath 105, which then may be retracted into the outer sheath 104 before removing the collector device 100 from the specimen collection location 302.

Once the specimen collection device 100 is inserted to appropriate depth, the actuator 102 is used to deploy the specimen collector 106. Once the specimen collector 106 and inner sheath 105 exits the outer sheath 104, the actuation mechanism 114 releases the inner sheath 105, thereby freeing the specimen collector 106 to move independently from the inner sheath 105. As the user moves the actuator 102 the specimen collector 106 moves relative to the inner sheath 105 and begins approaching the cap 108. The cap 108 is positioned at the terminal end of the inner sheath 105 and is articulated to enable the specimen collector 106 to move from the interior volume of the inner sheath 105 to a volume exterior to the specimen-collection device 100. The cap 108 also prevents the interior of the inner sheath 105 from being in communication with the volume exterior to the device 100, when the specimen collector 106 is not in its extended position. At some point (preferably before the specimen collector 106 contacts the cap 108), the actuation mechanism 114 opens the cap 108, thereby breaking seal 110, while allowing the specimen collector 106 to continue moving forward toward the specimen collection site 302 by the actuator 102. Thus, the specimen collector 106 moves through the aperture created by the opening of the cap 108 and out of the inner sheath 105.

While the specimen collector 106 is retained inside of the inner sheath 105, it is protected from contamination by seal 110. By the act of fully deploying the actuator 102, the user may move the specimen collector 106 from the protection of the inner sheath 105 to an exposed configuration. This facilitates contact with specific specimens to be collected. The specimen collector 106, configured in its extended position in the body cavity, may contact materials therein that might be present without contamination or dilution from surfaces outside of the specimen collection location 302. Further, or alternate actuation of the actuator 102 (e.g. rotation of the actuator 102 about its longitudinal axis), may allow for movement of the operational, distal, end of the specimen collector 106 so that it collects material from its immediate environment (e.g. from the walls of a body cavity, and/or other surfaces). The user may then use the actuator 102 to release the lock, and/or retract the specimen collector 106 back into the inner and outer sheaths 105 and 104 into its retracted position. The cap 108 and seal 110 seals the interior volume of the inner sheath 105 so that while the cap 108 is closed, the specimen collector 106 remains inside of the inner sheath 105 and protected from contamination and dilution.

Embodiments of the specimen-collection device and the method of its use may enable all portions of the specimen-collection device, save for the outer sheath, to be completely withdrawn from the interior volume of the outer sheath, while the outer sheath remains inside of the body cavity (or other specimen collection site). Furthermore, in some such embodiments, additional and/or different configurations of the specimen-collection device (lacking the outer sheath) may then be inserted into and removed from the specimen collection site through the outer sheath, which remains inside of the body cavity (or other specimen collection site). These embodiments allow for multiple, separate, specimen collections and/or alternate functions provided for by embodiments of the specimen-collection device described herein, to take place without the need for more than a single penetration. This allows for increased comfort for the subject being penetrated.

Figure 20:
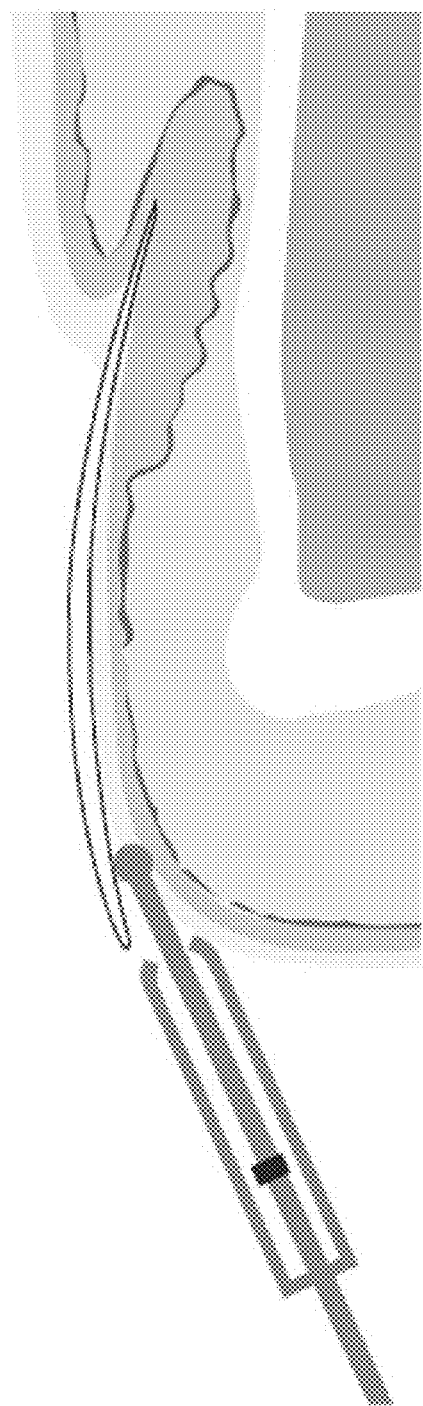
FIG. 20 depicts the use of a specimen-collection device, wherein the outer sheath has been removed, to collect a specimen from a specimen collection site underneath a fingernail or toenail.
Figure 21:
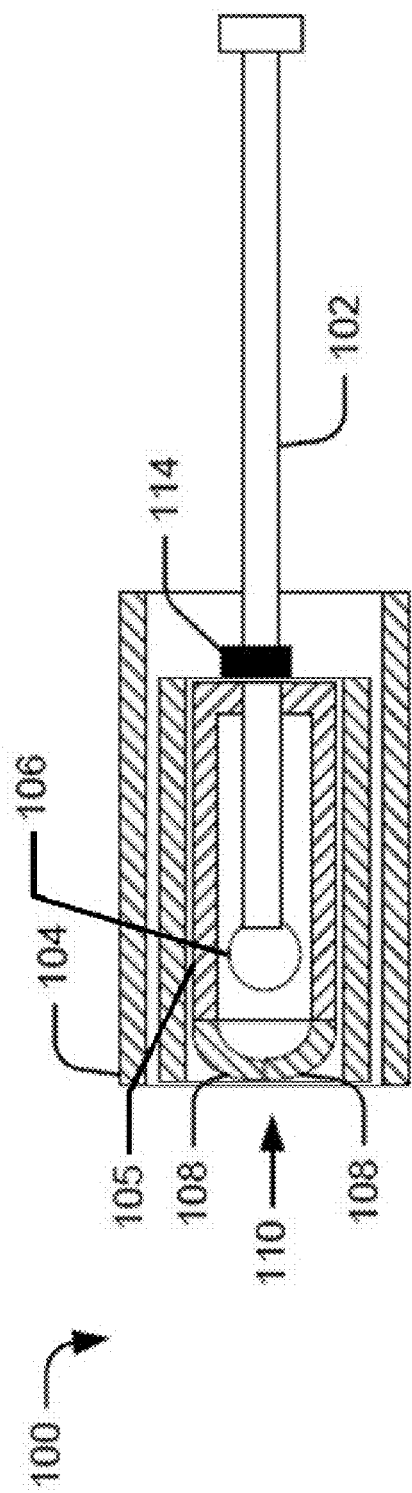
FIG. 21 depicts an exemplary embodiment of a specimen-collection device wherein there are more than one inner sheaths that may extend and retract from one another and from the outer sheath in response to actuation of the actuator.

Other embodiments of the specimen-collection device and the method of its use may provide for use of specimen-collection devices lacking their outer sheaths to be used for the collection of specimens, as exemplified in FIG. 20.

Specimens collected in devices with seals, such as seal 110, are less likely to dry out after collection since residual moisture will be retained in the sealed environment of the interior volume of the inner sheath 105. Embodiments of the specimen-collection device 100 may omit the seal 110 or be otherwise configured to allow the collected specimen to dry out for long-term specimen preservation, which may be important to the viability of DNA analysis. In one such embodiment, the interior volume of the inner sheath 105 may contain a desiccant located in a position that does not interfere with or otherwise influence specimen collection activities while still being able to draw moisture from the specimen to best insure its integrity.

FIG. 1 illustrates one arrangement of the cap 108 as being hinged. Further embodiments provide for a cap 108 that may be arranged in any number of other configurations. For example, in an alternate embodiment, the cap 108 could slide relative to the longitudinal axis of the specimen-collection device 100 so that the linear movement of the actuator 102 causes the cap 108 to open or close.

Some embodiments of the specimen-collection device may additionally comprise a lock to ensure that the specimen collector 106 remains in its retracted position, after collection of a specimen, until such time that the collected specimen is analyzed. In one embodiment, the lock may be configured to allow the actuator 102 to only actuate the device once, and then latch or lock the device in its closed configuration following the actuator's 102 retraction of the specimen collector 106 into the inner sheath 105. In this way, the present disclosure provides a means for attempting prevention or identification of attempts to tamper with the collected material. The present disclosure and the inherent security features may be used to corroborate the CoC of the specimen in the event that the specimen is to be used as evidence. In addition to, or alternatively, embodiments may provide for a lock configured to releasably lock the specimen collector 106 in its extended position. If so, the device could be manipulated while extended and locked to facilitate the deposition, manipulation, application, collection, etc. of material in situ.

In some embodiments, the specimen-collection device may be configured for self-collection. Self-collection allows for a multitude of benefits. Having the specimen-collection device configured for self-collection may allow for collection of specimens, likely containing DNA evidence, immediately after a sexual assault. Accordingly, this increases the probability of successful collection of a specimen potentially containing viable DNA that may allow for the determination of a perpetrator's DNA profile. The ability of the device to be configured for self-collection may additionally allow for collection of specimens when access to an appropriate medical, legal, or forensic facility is difficult or unavailable. For the victim of a sexual assault a specimen-collection device configured for self-collection would enable them to collect a specimen in a timely manner no matter where they may be. Due to the limited funding and geographic constraints for many individuals, there is a present lack of availability of professionals trained to collect specimens. A specimen-collection device configured for self-collection would allow individuals in any setting (i.e. rural, suburban, in theater) to collect and secure bodily fluids and/or other DNA-containing material(s) without the intervention of additional individuals. Furthermore, by facilitating self-collection, embodiments of the specimen-collection device may allow for specimen collection in an environment that is more comfortable for the individual collecting the specimen than would otherwise be available. This is of particular importance given the inherently traumatic nature of sexual assault, as well as the potentially traumatic specimen collection procedure.

The size and shape of the specimen-collection device 100 may be configured such that it can facilitate self-collection of specimens. For example, the distal end of the device may be rounded (as can all edges of such devices) to allow for easier, more comfortable insertion into various body cavities. Additionally, the position of the handle or actuator 102 positioned at the proximal end of the device (as in many embodiments), may enable self-collecting users to grasp the handle with relative ease. The simple linear action of actuator 102 of various embodiments also facilitates self-collection of specimens. The inner 104 and outer 105 sheaths protect the specimen collector 106 (and/or the collected specimen) from contamination even if the user experiences some difficulty in using the specimen-collection device 100.

The validity of evidence secured by self-collection of specimens constituting evidence using the specimen-collection device may benefit from additional structures incorporated into the specimen-collection device that may allow for the identification, recordation, and transmission of information related to the devices use. This information may serve as evidence corroborating the specimen collection and track the device for CoC, CPT, UDI, and inventory control purposes.

All of the electronics (e.g. power supply, battery, etc.) may be housed within the specimen-collection device 100 or otherwise incorporated into the device's construction. These electronic components may operate on low voltage power. Additionally, the electronics may be housed within a portion of the specimen-collection device 100 that may be closed, sealed, and/or locked by the lock provided for in some embodiments. As a result, the electronics may be protected from tampering, damage, etc. In some embodiments the packaging for the device may include the electronics that may trigger the identification and recordation of a DTLS related to use of the specimen-collection device 100.

All portions of specimen-collection devices 100 and aspects of the embodiments that might come into contact with the body, internal organs, tissues, structures, fluids, etc. of the user may be cleaned to (or beyond) an appropriate industry practice standard. Additionally, any portion of the specimen-collection device 106 of embodiments that comes into contact with the subject's body may be made from biocompatible materials (e.g. stainless steel, titanium, etc.). Some embodiments provide for devices in which all of the corners, edges, etc. that might contact a user's body are rounded and deburred resulting in surfaces polished to a smoothness sufficient to ensure safety and to avoid irritating or injuring sensitive tissue.

In addition, embodiments of the specimen-collection device may be designed to be disposable, wherein the device is disposed of after a specimen has been collected and/or subsequently analyzed.

Embodiments of the specimen-collection device may enable a portion of the collected specimen to remain in a protected state, free from contamination, dilution, and/or degradation, and within a CoC even after the specimen has been analyzed per medical and/or laboratory SOPs.

Embodiments of the disclosed specimen-collection device may include a means to prevent, or reduce, the likelihood of successful tampering with, or violation of, the specimen-collection device, or any specimen retained inside the device, after collection. Tamper-proofing measures may be enhanced by the integration of dielets, and/or a lock coupled to the specimen collector and/or the inner sheath of the specimen-collection device. Such a dielet and/or lock may be adapted to lock the inner sheath(s) of the specimen-collection device, or the specimen collector in their retracted, closed, and secured position. In contrast, when the lock is in its unlocked position, the specimen collector may move to its extended position, and be fixed in said extended position to ensure accurate specimen collection.

Embodiments of the specimen-collection device may include a seal arranged relative to the specimen collector and inner sheath in order to seal the specimen collector within the inner sheath when the specimen collector is in its retracted position; thereby sealing the collected specimen inside of the inner sheath's protected interior volume. This process of securing the collected specimen within the closed, sealed interior volume of the inner sheath protects the specimen from contamination, dilution, and/or degradation during its collection, transportation, and storage.

Embodiments of the specimen-collection device may include a light, which may either be detachable or otherwise affixed on embodiments of the specimen-collection device. Such a light may be used to facilitate the observation and/or recording of the specimen to be collected.

In one embodiment, a portion (or portions) of the specimen-collection device may be made of a transparent material in order to facilitate observation and/or recording of the specimen being collected during the collection process.

In accordance with disclosed embodiments, specimen-collection devices may be used to preserve evidence resulting from various types of incidents and make use of specimens obtained therewith. More specifically, many victims of sexual assault are (or become) too scared or embarrassed to report the incident. The victim may sometimes wait to report the incident thereby allowing contamination, dilution, or degradation of the specimens that might still be available. Furthermore, some authorities may discredit or discount minorities or discredit victim's accounts based on documented societal realities, thereby heightening these victims' reluctance. Despite their reluctance to report an incident, embodiments of the specimen-collection devices described herein would enable these individuals to collect the specimens themselves shortly after the incident. Once an individual is able to overcome their reluctance, they may then provide the specimen in the closed, sealed and locked device to law enforcement (or other authorities, e.g. Sexual Assault Response Team (SART) Center, or military officials) for analysis. The specimen stored in and protected by the inner sheath 105 could still allow for analysis of fluids, samples from skin surfaces, or other specimens collected to be analyzed for DNA, potentially leading to the successful identification of the perpetrator. Additionally, the DTL stamping of the specimen provided for by embodiments of the specimen-collection device may provide corroborating evidence of a victim's account of events (e.g. the collection of a specimen, or the sexual assault itself). As a result, independent third parties such as law enforcement, judges, military officials, insurance companies, and/or juries, etc. may have improved chances of resolving so-called he-said, she-said controversies.

Embodiments of the devices provided herein, furthermore, may be used as a base platform onto which other devices, attachments, tools, and/or accessories may be coupled.

In summary, the disclosure herein provides an explanation of how to make and use a specimen-collection device for observing, collecting, securing, and preserving DNA-containing material, which could potentially constitute evidence of a sexual assault. Embodiments of the specimen-collection device may comprise an outer sheath, an inner sheath, a specimen collector, an actuator, a cap, an actuation mechanism, a circuit, a memory, a processor, a switch, and a power source. The outer sheath may have a generally oblong shape for insertion into a human body cavity and an interior volume inside of which other parts of the specimen-collection device may be retained. The inner sheath may be disposed of inside of the interior volume of the outer sheath, and may be movable such that it may extend partially outside of the inner volume of the outer sheath in a telescoping fashion. The interior volume of the inner sheath may be configured to retain the specimen collector and any specimens it has collected, in a sealed environment while the inner sheath is closed. The specimen collector may be disposed inside of the interior volume of the inner sheath, and may be movable such that it may extend partially outside of the interior volume of the inner sheath in a telescoping fashion. The actuator is a portion of the specimen-collection device that may be operated by the user of the device. Actuation of the actuator may cause the actuation mechanism to extend the inner sheath from the interior volume of the outer sheath, and further (or an alternate method of) actuation of the actuator may cause the actuation mechanism to open the cap and extend the specimen collector from the interior volume of the inner sheath. The actuation mechanism may also cause the closing of the cap, and retraction of the specimen collector and inner sheath, when the actuator is actuated in reverse. The cap may be positioned at the end of the inner sheath. The cap may be openable to allow for the specimen collector to extend from the interior volume of the inner sheath, and it may be closeable to allow for the specimen collector and any collected specimen to be sealed inside of the interior volume of the inner sheath, thereby protecting the collected specimen from contamination, dilution, and degradation. The circuit may identify information related to the operation of the specimen-collection device; including information related to the time and date of the specimen-collection device's use, the location where the specimen-collection device was used, and security information. The circuit may identify such information in response to the activation of the switch. Activation of the switch may be triggered by actuation of the actuator, opening and/or closing of the cap, or any number of other actions associated with operation of the specimen-collection device. The processor may take the information identified by the circuit in response to activation of the switch and transfer it to the memory. The memory may record the information identified by the circuit. The power source may provide electrical power to the electronic components of the specimen-collection device.

It is important to note that while the device and methods detailed above are discussed with specific reference to the collection of biologic specimens potentially constituting evidence related to sexual assault, persons having ordinary skill in the art will understand that such devices and methods can be applied to any number of scenarios (e.g. other forensic evidence collection, medical procedures including surgical procedures, environmental sampling, food sampling, etc.).

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope of the disclosure unless otherwise claimed. No language in the specification should be construed as indicating any non-claimed element as essential to the practice of the disclosure as used herein.

What is claimed is:

1. A specimen-collection device for observing, collecting, securing, and preserving DNA-containing material potentially constituting evidence of a sexual assault, said device comprising:
    an outer sheath for insertion into a human body cavity, said an outer sheath having an oblong shape, an interior volume, and a longitudinal axis;
    an inner sheath for retaining a specimen collector and specimen in a sealed environment, disposed within said inner volume of said outer sheath, said inner sheath having an interior volume, wherein said inner sheath is movable along said longitudinal axis into and from said interior volume of said outer sheath;
    a specimen collector for collecting specimens comprising DNA-containing material, said specimen collector disposed within said interior volume of said inner sheath, wherein said specimen collector is movable along said longitudinal axis into and from said interior volume of said inner sheath;
    a cap for preventing exposure of said interior volume of said inner sheath to a volume exterior to said specimen-collection device when said cap is in a closed configuration, said cap coupled to an end of said inner sheath, wherein said cap is openable to accommodate passage of said specimen collector to said volume exterior to said specimen-collection device when said specimen collector is in an extended position, and wherein said cap is closeable to prevent exposure of said specimen collector to the volume exterior to said specimen-collection device when said specimen collector is in a retracted position;
    an actuation mechanism for moving said inner sheath into and from said interior volume of said outer sheath, for moving said specimen collector into and from said interior volume of said inner sheath, and for opening and closing said cap to accommodate movement of said specimen collector, said actuation mechanism being arranged relative to an actuator, said cap, said specimen collector, said inner sheath, and said outer sheath;
    said actuator for operating said actuation mechanism, wherein said actuator is coupled to said actuation mechanism, whereby actuation of the actuator engages said actuation mechanism and moves said inner sheath and said specimen collector along said longitudinal axis between an inner sheath retracted position and an inner sheath extended position and a first specimen collector retracted position and a first specimen collector extended position relative to said outer sheath, and the actuator configured for additional actuation to engage said actuation mechanism, said specimen collector movable along said longitudinal axis between a second specimen collector retracted position and a further specimen collector extended position relative to said inner sheath by the additional actuation of the actuation mechanism;
    a circuit for identifying information related to use of said specimen-collection device, said information comprising one or more parameters selected from the group consisting of:
        a time for establishing the time when said specimen-collection device is used to collect a specimen;
        a location for establishing the location of said specimen-collection device when said specimen-collection device is used to collect a specimen;
        a date value for establishing a year, month, and day when said specimen-collection device is used to collect a specimen; and
        security information for determining whether a specimen collected by said specimen-collection device has been accessed, or otherwise tampered with, after its collection;
    a memory for recording said information related to use of said specimen-collection device identified by said circuit;
    a processor for transferring said information related to use of said specimen-collection device from said circuit to said memory;

a switch for triggering said circuit to identify said information related to use of said specimen-collection device, and for triggering said information related to use of said specimen-collection device to be recorded in said memory; and a power source for supplying electrical power to said circuit, said processor, and said memory, said power source being electrically connected to said circuit, said processor, and said memory.

2. A specimen-collection device for the collection organic, inorganic, and non-organic material, said device comprising:

an outer sheath having an oblong shape, an interior volume, and a longitudinal axis;

an inner sheath having an interior volume, disposed within said inner volume of said outer sheath, wherein said inner sheath is movable along said longitudinal axis into and from said interior volume of said outer sheath;

a specimen collector disposed within said interior volume of said inner sheath, wherein said specimen collector is movable along said longitudinal axis into and from said interior volume of said inner sheath;

a cap coupled to an end of said inner sheath, wherein said cap is openable to accommodate passage of said specimen collector to a volume exterior to said interior volume of said inner sheath when said specimen collector is in said extended position, and wherein said cap is closeable to prevent exposure of said specimen collector to the volume exterior to said specimen-collection device when said specimen collector is in said retracted position;

an actuation mechanism for moving said inner sheath into and from said interior volume of said outer sheath, for moving said specimen collector into and from said interior volume of said inner sheath, and for opening and closing said cap to accommodate movement of said specimen collector; and an actuator for operating said actuation mechanism, wherein said actuator is coupled to said actuation mechanism, whereby actuation of the actuator engages said actuation mechanism and moves said inner sheath and said specimen collector along said longitudinal axis between an inner sheath retracted position and an inner sheath extended position and a first specimen collector retracted position and a first specimen collector extended position relative to said outer sheath, and the actuator configured for additional actuation to engage said actuation mechanism, said specimen collector movable along said longitudinal axis between a second specimen collector retracted position and a further specimen collector extended position relative to said inner sheath by the additional actuation of the actuation mechanism.

3. The specimen-collection device of claim 2, further comprising:

a circuit for identifying information related to use of said specimen-collection device, said information related to use of said specimen-collection device comprising one or more parameter selected from the group consisting of:
a time;
a location;
a date; and
security information;

a memory in communication with said circuit, wherein said memory is configured to record said information identified by said circuits;

a processor in communication with said circuit and said memory, said processor operable to transfer said information from said circuit to said memory;

a switch coupled to said circuit, wherein activation of said switch causes said information related to use of said specimen-collection device to be identified by said circuit and recorded in said memory; and a power source in electrical communication with said circuit, said processor, and said memory, wherein said power source is configured to supply electrical power to said circuit, processor, and memory.

4. The specimen-collection device of claim 3, further comprising a transmitter in communication with said processor, wherein said transmitter is configured to transmit said information related to use of said specimen-collection device identified by said circuit through a network to a remote computing device.

5. The specimen-collection device of claim 3, wherein said circuit, memory, processor, and power source are contained within the structure of said specimen-collection device.

6. The specimen-collection device of claim 3, wherein said security information enables said specimen-collection device to be uniquely identifiable.

7. The specimen-collection device of claim 2, wherein said outer sheath has a diameter ranging between one sixteenth of an inch and six inches, inclusive of the minimum and maximum values.

8. The specimen-collection device of claim 2, further comprising one or more additional inner sheaths, said one or more additional inner sheaths having progressively decreasing dimensions, and wherein said more than one inner sheaths having progressively decreasing dimensions are disposed of inside of and extendable from one another in a telescoping fashion.

9. The specimen-collection device of claim 2, wherein said inner sheath, said specimen collector, said cap, said actuation mechanism, and said actuator are removable from and insertable into said outer sheath.

10. The specimen-collection device of claim 2, wherein said specimen collector has a length ranging between one sixteenth of an inch and seven inches, inclusive of the minimum and maximum values.

11. The specimen-collection device of claim 2, wherein said actuator has a length between one half of an inch and eleven inches, inclusive of the minimum and maximum values.

12. The specimen-collection device of claim 2, wherein said device is configured for self-collection.

13. The specimen-collection device of claim 2, further comprising a lock coupled to said cap, wherein said lock is configured to secure said device in said retracted position.

14. The specimen-collection device of claim 2, wherein said actuator is actuated electrically.

15. The specimen-collection device of claim 2, further comprising a seal arranged between said inner sheath and said cap, whereby said seal prevents said specimen collector from being in contact with a volume external to said interior volume of said inner sheath when said cap is in a closed position.

16. The specimen-collection device of claim 15, wherein said light is detachable from said specimen-collection device.

17. The specimen-collection device of claim 2, wherein said actuator comprises a rod having a handle, and wherein said rod is fixedly attached to said specimen collector.

18. The specimen-collection device of claim 2, further comprising a light.

19. The specimen-collection device of claim 2, wherein said specimen-collection device is disposable after a single use.

20. The specimen-collection device of claim 2, wherein said specimen collection device is sterilizable and reusable.

21. The specimen-collection device of claim 2, wherein a portion of said specimen-collection device is made of a transparent material.

22. The specimen-collection device of claim 2, wherein said device comports with UDI regulations as defined by the FDA.

23. A method of collecting specimens using a specimen-collection device comprising:

determining a specimen collection site;

placing a specimen-collection device in proximity to said specimen collection site while the specimen collector portion of said specimen-collection device is in an compact and unexposed state;

actuating said specimen-collection device, whereby said actuation of said specimen-collection device causes a second portion of the specimen-collection device to extend from a first portion of the specimen-collection device, wherein the specimen collector portion remains unexposed throughout the actuating step;

exposing said specimen collector portion of said specimen-collection device when in proximity to said specimen collection site;

collecting a specimen located at said specimen collection site by making physical contact between said specimen collector portion of said specimen-collection device and a specimen located at said specimen collection site;

identifying information related to said collection of the specimen from said specimen collection site using circuits of said specimen-collection device;

recording said information related to said collection of the specimen from said specimen collection site using a processor and a memory of said specimen-collection device;

returning said specimen collector portion of said specimen-collection device to an unexposed position when in proximity to said specimen collection site;

un-actuating said specimen-collection device, whereby said un-actuation of said specimen-collection device causes the second portion of the specimen-collection device to return into the first portion of the specimen-collection device, wherein the specimen collector portion remains unexposed throughout the un-actuating step; and removing said specimen-collection device from proximity to said specimen collection site.

24. The method of claim 23, wherein said specimen collector portion of said specimen-collection device is only exposed while in proximity to said specimen collection site.

25. The method of claim 23, further comprising using said identified and recorded information related to said collection of said specimen from said specimen collection site to corroborate an account of said collection using said processor and said memory of said specimen-collection device.

26. The method of claim 23, wherein said specimen collection site comprises a surface.

27. The method of claim 23, wherein said specimen collection site comprises a body cavity.

* * * * *